(12) United States Patent
Kessler et al.

(10) Patent No.: US 11,696,896 B2
(45) Date of Patent: Jul. 11, 2023

(54) IMMUNOMODULATORY NANOPARTICLE TREATMENT OF BRAIN INJURY

(71) Applicant: Northwestern University, Evanston, IL (US)

(72) Inventors: John A. Kessler, Evanston, IL (US); Sripadh B. Sharma, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 17/076,235

(22) Filed: Oct. 21, 2020

(65) Prior Publication Data

US 2021/0121413 A1   Apr. 29, 2021

Related U.S. Application Data

(60) Provisional application No. 62/924,849, filed on Oct. 23, 2019.

(51) Int. Cl.
*A61K 9/51* (2006.01)
*A61K 9/00* (2006.01)

(52) U.S. Cl.
CPC .......... *A61K 9/5153* (2013.01); *A61K 9/0019* (2013.01)

(58) Field of Classification Search
CPC .................................................. A61K 9/5153
See application file for complete search history.

(56) References Cited

U.S. PATENT DOCUMENTS

| | | | | |
|---|---|---|---|---|
| 2008/0014285 A1* | 1/2008 | Di Mauro | ............ | A61K 31/425 424/617 |
| 2014/0303041 A1* | 10/2014 | Hayes | ............ | C07K 16/18 506/18 |

FOREIGN PATENT DOCUMENTS

WO   WO-2020056323 A1 *   3/2020   ......... A61K 31/7088

OTHER PUBLICATIONS

Raj Putatunda, John R. Bethea, Wen-Hui Hu. "Potential immunotherapies for traumatic brain and spinal cord injury." Chinese Journal of Traumatology, vol. 21, (2018), pp. 125-136, available online Apr. 18, 2018. (Year: 2018).*
Su Ji Jeong et al. "Intravenous immune-modifying nanoparticles as a therapy for spinal cord injury in mice." Neurobiology of Disease, vol. 108, (2017), pp. 73-82. (Year: 2017).*
Vimala N. Bharadwaj et al. "Temporal assessment of nanoparticle accumulation after experimental brain injury: Effect of particle size." Scientific Reports, 6:29988 | DOI: 10.1038/srep29988, 2016, pp. 1-12. (Year: 2016).*
National Institute of Child Health and Development. "What are the parts of the nervous system?." https://www.nichd.nih.gov/health/topics/neuro/conditioninfo/parts accessed Jul. 29, 2022, 4 printed pages. (Year: 2022).*
Alan I. Faden et al. "Progressive inflammation-mediated neurodegeneration after traumatic brain or spinal injury." British Journal of Pharmacology, vol. 173, 2016, pp. 681-691. (Year: 2016).*
Peter E. Batchelor, Simon Tan, Taryn E. Wills, Michelle J. Porritt, and David W. Howells. "Comparison of Inflammation in the Brain and Spinal Cord following Mechanical Injury." Journal of Neurotrauma, vol. 25, Oct. 2008, pp. 1217-1225. (Year: 2008).*

(Continued)

*Primary Examiner* — Isaac Shomer

(74) *Attorney, Agent, or Firm* — Foley & Lardner LLP

(57) ABSTRACT

Provided herein are immunomodulatory nanoparticles, compositions containing the same, and methods of use thereof, such as for the treatment of traumatic brain injury.

17 Claims, 26 Drawing Sheets

(56) References Cited

OTHER PUBLICATIONS

Luis J. Cruz et al. "Effect of PLGA NP size on efficiency to target traumatic brain injury." Journal of Controlled Release, vol. 223, 2016, pp. 31-41. (Year: 2016).*
Sripadh Sharma et al. "Intravenous Immunomodulatory Nanoparticle Treatment for Traumatic Brain Injury." Annals of Neurology, vol. 87, 2020, pp. 442-455. (Year: 2020).*
Gao, X. et al., "Mild Traumatic Brain Injury Results in Extensive Neuronal Degeneration in the Cerebral Cortex", J Neuropathol Exp Neurol., Mar. 2011, vol. No. 70, Issue No. 3, pp. 183-191.
Kakulas, B.A. et al., "White matter changes in human spinal cord injury", in Stalberg, E. et al. (Eds.), Spinal Cord Monitoring, 1998, Springer, Vienna.

* cited by examiner

IMMUNOMODULATORY NANOPARTICLE TREATMENT OF BRAIN INJURY

CROSS-REFERENCE TO RELATED APPLICATIONS

This application claims the benefit of U.S. Provisional Patent Application No. 62/924,849, filed Oct. 23, 2019, the content of which is incorporated by reference herein in its entirety.

STATEMENT OF GOVERNMENT SUPPORT

This invention was made with government support under Grant No. 1 F31 NS105451-01A1 awarded by the National Institutes of Health (NIH). The government has certain rights in the invention.

FIELD

The present invention relates generally to the field of immunomodulatory nanoparticles and uses thereof for traumatic brain injury.

SUMMARY

Provided herein, in one aspect, are methods of treating traumatic brain injury in a subject in need thereof, the methods comprising administering to the subject a therapeutically effective amount of nanoparticles consisting essentially of poly(lactic-co-glycolic acid) (PLGA). In some embodiments, the nanoparticles are carboxylated. In some embodiments, the nanoparticles have a diameter in a range of between about 300 nm and about 1 µm. In some embodiments, the nanoparticles have a diameter of about 500 nm. In some embodiments, the nanoparticles are free of any attached or embedded peptide, antigen, or other active agent. In some embodiments, the nanoparticles consist of PLGA. In some embodiments, the nanoparticles are administered at least once per day. In some embodiments, the nanoparticles are administered intravenously.

Provided herein, in another aspect, are methods of reducing secondary inflammatory damage in the brain after traumatic brain injury in a subject in need thereof, the methods comprising administering to the subject a therapeutically effective amount of nanoparticles consisting essentially of poly(lactic-co-glycolic acid) (PLGA). In some embodiments, the nanoparticles are carboxylated. In some embodiments, the nanoparticles have a diameter in a range of between about 300 nm and 1 µm. In some embodiments, the nanoparticles have a diameter of about 500 nm. In some embodiments, the nanoparticles are free of any attached or embedded peptide, antigen, or other active agent. In some embodiments, the nanoparticles consist of PLGA. In some embodiments, the nanoparticles are administered at least once per day. In some embodiments, the nanoparticles are administered intravenously.

Provided herein, in another aspect, are methods of limiting lesion volume in the brain after traumatic brain injury in a subject in need thereof, the methods comprising administering to the subject a therapeutically effective amount of nanoparticles consisting essentially of poly(lactic-co-glycolic acid) (PLGA). In some embodiments, the nanoparticles are carboxylated. In some embodiments, the nanoparticles have a diameter in a range of between about 300 nm and 1 µm. In some embodiments, the nanoparticles have a diameter of about 500 nm. In some embodiments, the nanoparticles are free of any attached or embedded peptide, antigen, or other active agent. In some embodiments, the nanoparticles consist of PLGA. In some embodiments, the nanoparticles are administered at least once per day. In some embodiments, the nanoparticles are administered intravenously.

Provided herein, in another aspect, are methods of attenuating brain edema after closed-head injury in a subject in need thereof, the methods comprising administering to the subject a therapeutically effective amount of nanoparticles consisting essentially of poly(lactic-co-glycolic acid) (PLGA). In some embodiments, the nanoparticles are carboxylated. In some embodiments, the nanoparticles have a diameter in a range of between about 300 nm and 1 µm. In some embodiments, the nanoparticles have a diameter of about 500 nm. In some embodiments, the nanoparticles are free of any attached or embedded peptide, antigen, or other active agent. In some embodiments, the nanoparticles consist of PLGA. In some embodiments, the nanoparticles are administered at least once per day. In some embodiments, the nanoparticles are administered intravenously.

DETAILED DESCRIPTION

Figure 1:
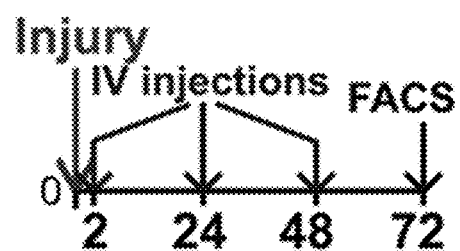
FIG. 1 depicts a non-limiting example of experimental design for administration of an exemplary nanoparticle of the present invention in murine controlled cortical impact (CCI) model. Injections were via lateral tail vein route.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

Definitions

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. For example, the term "a cell" includes one or more cells, including mixtures thereof. "A and/or B" is used herein to include all of the following alternatives: "A," "B," "A or B," and "A and B."

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "PLGA" refers to poly(lactic-co-glycolic acid) or poly(D,L-lactide-co-glycolide). Unless otherwise noted, all references to PLGA herein include references to pharmaceutically acceptable salts, solvates, and isotopically labeled versions thereof. Also included within the scope provided herein are pharmaceutical compositions comprising pharmaceutically acceptable salts, solvates, and isotopically labeled versions of PLGA. In some embodiments, the PLGA has an L/G ratio of 50/50 and MW of 30,000.

As used herein, the terms "administration" and "administering" mean the delivery of a bioactive composition or formulation to a subject by an administration route including, but not limited to, intravenous, intra-arterial, intramuscular, intraperitoneal, subcutaneous, intramuscular, or combinations thereof. In some embodiments, the administration to a subject is intravenous.

As used herein, the term "subject" means a mammal, including, but not limited to, a human, a dog or a cat. In some embodiments, the subject is a human. In some embodiments, the subject is a dog. In some embodiments, the subject is a cat.

As used herein, the term "therapeutically effective amount" means that amount of the compound or compounds (e.g., nanoparticles disclosed herein), or pharmaceutically acceptable salts thereof, being administered to a subject which will relieve to some extent one or more of the symptoms of the disorder being treated.

Traumatic Brain Injury

Traumatic brain injury (TBI), a form of acquired brain injury, is a disruption in the normal function of the brain that can be caused by a bump, blow, or jolt to the head, or a penetrating head injury. Symptoms of a TBI may be mild, moderate, or severe, depending on the extent of damage to the brain. A person with mild TBI may remain conscious or may experience loss of consciousness for a few seconds or minutes. Other symptoms of mild TBI include headache, confusion, lightheadedness, dizziness, blurred vision or tired eyes, ringing in the ears, bad taste in the mouth, fatigue or lethargy, a change in sleep patterns, behavioral or mood changes, and trouble with memory, concentration, attention, or thinking. A person with a moderate of severe TBI may show these symptoms, but may also have a headache that gets worse or does not go away, repeated vomiting or nausea, convulsions or seizures, an inability to awaken from sleep, weakness or numbness in the extremities, loss of coordination, and increased confusion, restlessness, or agitation.

TBI is a major global and domestic health issue affecting more than (a grossly underestimated) 2.5 million people in the U.S every year with more than 5 million Americans currently living with at least one TBI-related sequela. Additionally, the prognosis of the patients that have received rehabilitation succeeding TBI is grim, as 20% of such patients will die over the upcoming 5 years. The most vulnerable patient populations (young children and the elderly) are statistically the most affected. Furthermore, the economic burden for direct and indirect costs of TBI are more than 76 billion dollars every year. Historically and currently, there are no definitive treatments for TBI once the injury has occurred as prevention is the number one abrogating method. After the primary trauma, secondary injury, largely mediated by blood-borne immune cells called monocytes, takes place, causing damage to surrounding healthy cells. Furthermore, cellular and whole brain swelling (edema) resulting from this secondary injury causes increased intracranial pressure increasing risk of (and often causing) irreversible brain damage and death. In clinical settings, hyperventilation, hyperosmotic solution infusion, and hypothermia are used with unclear success.

Immunosuppression such as intravenous methylprednisolone for spinal cord injury (SCI) has been a contentious topic in central nervous system (CNS) injury, giving equivocal results in both preclinical and clinical trials. Because the immune system is such a broad and diverse set of cell populations, immunomodulation of specific cell types may be the next step in exploring attenuation of neuroinflammation succeeding TBI, with hopes of reducing the amount of secondary damage. Even still, the targeting of specific immune cells in TBI has not been perfect. Materials such as clodronate liposomes and the like are too nonspecific and give a broad-spectrum immunosuppression. Antibodies to specific cell types are difficult to store, measure, dose and deliver when needed in an emergent setting.

Methods

In one aspect, provided herein is a method of treating traumatic brain injury in a subject in need thereof, the method comprising, consisting essentially of, or consisting of administering to the subject a therapeutically effective amount of immunomodulatory nanoparticles (IMPs). Without being bound to any one particular theory, it is believed that IMPs change the overall neuroinflammatory response by altering the number and the pro-inflammatory phenotype of cells infiltrating the brain, which impact the capacity of these cells to sustain an inflammatory response as well as direct the recruitment of additional immune cells.

In another aspect, provided herein is a method of treating traumatic brain injury in a subject in need thereof, the method comprising, consisting essentially of, or consisting of administering to the subject a therapeutically effective amount of nanoparticles consisting essentially of poly(lactic-co-glycolic acid) (PLGA).

In another aspect, provided herein is a method of treating traumatic brain injury in a subject in need thereof, the method comprising, consisting essentially of, or consisting of administering to the subject a therapeutically effective amount of nanoparticles consisting essentially of carboxylated poly(lactic-co-glycolic acid) (PLGA).

In another aspect, provided herein is a method of reducing secondary inflammatory damage in the brain after traumatic brain injury in a subject in need thereof, the method comprising, consisting essentially of, or consisting of administering to the subject a therapeutically effective amount of IMPS.

In another aspect, provided herein is a method of reducing secondary inflammatory damage in the brain after traumatic brain injury in a subject in need thereof, the method comprising, consisting essentially of, or consisting of administering to the subject a therapeutically effective amount of nanoparticles consisting essentially of PLGA.

In another aspect, provided herein is a method of reducing secondary inflammatory damage in the brain after traumatic brain injury in a subject in need thereof, the method comprising, consisting essentially of, or consisting of administering to the subject a therapeutically effective amount of nanoparticles consisting essentially of carboxylated PLGA.

In another aspect, provided herein is a method of reducing a population of pro-inflammatory macrophages in the brain after traumatic brain injury in a subject in need thereof, the method comprising, consisting essentially of, or consisting of administering to the subject a therapeutically effective amount of IMPS.

In another aspect, provided herein is a method of reducing a population of pro-inflammatory macrophages in the brain after traumatic brain injury in a subject in need thereof, the method comprising, consisting essentially of, or consisting of administering to the subject a therapeutically effective amount of nanoparticles consisting essentially of PLGA.

In another aspect, provided herein is a method of reducing a population of pro-inflammatory macrophages in the brain after traumatic brain injury in a subject in need thereof, the method comprising, consisting essentially of, or consisting of administering to the subject a therapeutically effective amount of nanoparticles consisting essentially of carboxylated PLGA.

In another aspect, provided herein is a method of limiting lesion volume in the brain after traumatic brain injury in a subject in need thereof, the method comprising, consisting essentially of, or consisting of administering to the subject a therapeutically effective amount of IMPs.

In another aspect, provided herein is a method of limiting lesion volume in the brain after traumatic brain injury in a subject in need thereof, the method comprising, consisting essentially of, or consisting of administering to the subject a therapeutically effective amount of nanoparticles consisting essentially of PLGA.

In another aspect, provided herein is a method of limiting lesion volume in the brain after traumatic brain injury in a subject in need thereof, the method comprising, consisting essentially of, or consisting of administering to the subject a therapeutically effective amount of nanoparticles consisting essentially of carboxylated PLGA.

In another aspect, provided herein is a method of attenuating brain edema after closed-head injury in a subject in need thereof, the method comprising, consisting essentially of, or consisting of administering to the subject a therapeutically effective amount of IMPs.

In another aspect, provided herein is a method of attenuating brain edema after closed-head injury in a subject in need thereof, the method comprising, consisting essentially of, or consisting of administering to the subject a therapeutically effective amount of nanoparticles consisting essentially of PLGA.

In another aspect, provided herein is a method of attenuating brain edema after closed-head injury in a subject in need thereof, the method comprising, consisting essentially of, or consisting of administering to the subject a therapeutically effective amount of nanoparticles consisting essentially of carboxylated PLGA.

Immunomodulatory Nanoparticles (IMPs)

The immunomodulatory nanoparticles (also referred to as "nanoparticles" herein) of the present disclosure comprise, consist essentially of, or consist of PLGA. In some embodiments, the nanoparticles are carboxylated. In some embodiments, the nanoparticles are not carboxylated. In some embodiments, the nanoparticles are negatively charged.

Nanoparticles of the present disclosure may have a diameter in a range of between about 300 nm and about 1 μm. This includes ranges of about 300 nm to about 900 nm, about 300 nm to about 800 nm, about 300 nm to about 700 nm, about 300 nm to about 600 nm, about 300 nm to about 500 nm, about 400 nm to about 1 μm, about 400 nm to about 900 nm, about 400 nm to about 800 nm, about 400 nm to about 700 nm, about 400 nm to about 600 nm, about 400 nm to about 500 nm, about 500 nm to about 1 μm, about 500 nm to about 900 nm, about 500 nm to about 800 nm, about 500 nm to about 700 nm, or about 500 nm to about 600 nm.

In some embodiments, the diameter of the nanoparticles is about 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nm, including increments therein. In some embodiments, the diameter of the nanoparticles is at least about 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, or 990 nm, including increments therein.

In some embodiments, the nanoparticles are free of any attached or embedded peptide, antigen, or other active agent.

Compositions

In some embodiments, nanoparticles described herein are formulated as a pharmaceutically acceptable composition when combined with at least one pharmaceutically acceptable carrier and/or excipient. Such pharmaceutically acceptable carrier(s) and/or excipient(s) are non-toxic and do not interfere with the efficacy of active ingredient (e.g., the nanoparticles described herein). The precise nature of the pharmaceutically acceptable carrier(s) and/or excipient(s) depends on the route of administration. The compositions can be formulated for any pharmaceutically acceptable route of administration, such as for example, by oral, parenteral, pulmonary, topical, rectal, nasal, vaginal administration, or via implanted reservoir. Parenteral or systemic administration includes, but is not limited to, subcutaneous, intravenous, intraperitoneally, intramuscular, intra-articular, intra-synovial, intrasternal, intrathecal, intralesional and intracranial injections. The compositions disclosed herein may be formulated into preparations in solid, semi-solid, liquid or gaseous forms, such as powders, granules, solutions, suppositories, injections, inhalants and aerosols. In some embodiments, the nanoparticles disclosed herein are administered intravenously.

In pharmaceutical dosage forms, the nanoparticles disclosed herein may be administered in the form of their pharmaceutically acceptable salt, or the nanoparticles may also be used alone or in appropriate association, as well as in combination, with other pharmaceutically active compounds. The following methods and excipients are merely exemplary and are in no way limiting.

For systemic, intrathecal, topical, intranasal, or subcutaneous administration, formulations of the nanoparticles useful in the methods of the present invention may utilize conventional diluents, carriers, or excipients etc., such as are known in the art can be employed to deliver the nanoparticles. For example, the formulations may comprise one or more of the following: a stabilizer, a surfactant (such as a nonionic, ionic, anionic, cationic, or zwitterionic surfactant), and optionally a salt and/or a buffering agent. The nanoparticles may be delivered in the form of a solution or in a reconstituted lyophilized form.

In some embodiments, the stabilizer may, for example, be an amino acid, such as for instance, glycine or an oligosaccharide, such as for example, sucrose, tetralose, lactose or a dextran. Alternatively, the stabilizer may be a sugar alcohol, such as for instance, mannitol, sorbitol, xylitol, or a combination thereof. In some embodiments, the stabilizer or combination of stabilizers constitutes from about 0.1% to about 10% by weight of the formulation, or any percentage in between these two values.

In some embodiments, the surfactant is a nonionic surfactant, such as a polysorbate. Some examples of suitable surfactants include polysorbates (e.g., Tween20, Tween80); a polyethylene glycol or a polyoxyethylene polyoxypropylene glycol, such as Pluronic F-68 at from about 0.001% (w/v) to about 10% (w/v), or any percentage in between these two values.

A salt or buffering agent may be any salt or buffering agent, such as for example, sodium chloride, or sodium/potassium phosphate, respectively. In certain embodiments, the buffering agent maintains the pH of the pharmaceutical composition in the range of about 5.5 to about 7.5, or any pH in between these two values. The salt and/or buffering agent is also useful to maintain the osmolality at a level suitable for administration to a human or an animal. In some embodiments, the salt or buffering agent is present at a roughly isotonic concentration of about 150 mM to about 300 mM.

The formulations of the nanoparticles useful in the methods of the present invention may additionally comprise one or more conventional additives. Some non-limiting examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

The amount of any individual excipient in the composition will vary depending on the role of the excipient, the dosage requirements of the active agent component(s), and particular needs of the composition. Generally, however, the excipient will be present in the composition in an amount of about 1% to about 99% by weight, preferably from about 5% to about 98% by weight, more preferably from about 15 to about 95% by weight of the excipient. In general, the amount of excipient present in a composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

One or more additional active agents may be administered with nanoparticles disclosed herein, either sequentially or concomitantly. In some embodiments, the nanoparticles disclosed herein and the one or more additional active agents are administered within a single composition.

In some embodiments, nanoparticles disclosed herein can be administered to a patient in an effective amount ranging from about 0.001 mg/kg to about 100 mg/kg per day. This includes 0.001, 0.0025, 0.005, 0.0075, 0.01, 0.025, 0.05, 0.075, 0.1, 0.25, 0.5, 0.75, 1, 2, 3, 4, 5, 6, 7, 8, 9, 10, 15, 20, 25, 30, 35, 40, 45, 50, 55, 60, 65, 70, 75, 80, 85, 90, 95, or 100 mg/kg.

Generally, a therapeutically effective amount of a compound disclosed herein will range from a total daily dosage of about 0.1 mg/day to 1000 mg/day, about 30-720 mg/day, about 60-600 mg/day, or about 100-480 mg/day, or more. In some embodiments, a therapeutically effective amount of nanoparticles disclosed herein will range from about 1-240 mg/day, about 30-240 mg/day, about 30-200 mg/day, about 30-120 mg/day, about 1-120 mg/day, about 50-150 mg/day, about 60-150 mg/day, about 60-120 mg/day, or about 60-100 mg/day, administered as either a single dosage or as multiple dosages. In some embodiments, multiple dosages include two, three, or four doses per day.

In some embodiments, the therapeutically effective amount of nanoparticles disclosed herein is at least 0.1 mg/day, at least 0.5 mg/day, at least 1 mg/day, at least 5 mg/day, at least 10 mg/day, at least 20 mg/day, at least 30 mg/day, at least 40 mg/day, at least 50 mg/day, at least 60 mg/day, at least 70 mg/day, at least 80 mg/day, at least 90 mg/day, at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 225 mg/day, at least 250 mg/day, at least 275 mg/day, at least 300 mg/day, at least 325 mg/day, at least 350 mg/day, at least 375 mg/day, at least 400 mg/day, at least 425 mg/day, at least 450 mg/day, at least 475 mg/day, at least 500 mg/day, at least 525 mg/day, at least 550 mg/day, at least 575 mg/day, at least 600 mg/day, at least 625 mg/day, at least 650 mg/day, at least 675 mg/day, at least 700 mg/day, at least 725 mg/day, at least 750 mg/day, at least 775 mg/day, at least 800 mg/day, at least 825 mg/day, at least 850 mg/day, at least 875 mg/day, at least 900 mg/day, at least 925 mg/day, at least 950 mg/day, at least 975 mg/day, or at least 1000 mg/day.

In some embodiments, the subject receives an amount of the nanoparticles at least one a day. In some embodiments, the subject receives an amount of the nanoparticles once a day, twice a day, or three times a day. In some embodiments, the subject receives an amount of the nanoparticles every other day, every two days, or every three days. In some embodiments, the subject receives an amount of the nanoparticles once per week or twice per week. In some embodiments, the subject receives an amount of the nanoparticles once every other week. In some embodiments, the subject receives an amount of the nanoparticles twice per month. In some embodiments, the subject receives an amount of the nanoparticles once monthly, once every other month, once every two months, once every three months, once every four months, once every five months, or once every six months.

Of course, the dosage may be changed according to the patient's age, weight, susceptibility, symptom, or the efficacy of the compound.

The nanoparticles and compositions disclosed herein may be used to prepare formulations and medicaments that treat traumatic brain injury. In some embodiments, the nanoparticles and compositions disclosed herein may be used to prepare formulations and medicaments that reduce secondary inflammatory damage in the brain after traumatic brain injury. In some embodiments, the nanoparticles and compositions disclosed herein may be used to prepare formulations and medicaments that reduce a population of pro-inflammatory macrophages in the brain after traumatic brain injury. In some embodiments, the nanoparticles and compositions disclosed herein may be used to prepare formulations and medicaments that limit lesion volume in the brain after traumatic brain injury. In some embodiments, the nanoparticles and compositions disclosed herein may be used to prepare formulations and medicaments that attenuate brain edema after closed-head injury.

Kits

The nanoparticles and compositions disclosed herein may be provided in kits. The kits can further contain instructions to administer the nanoparticles and compositions disclosed herein. Such kits may be convenient to transport, store, dose, and administer the nanoparticles and compositions disclosed herein.

The present invention, thus generally described, will be understood more readily by reference to the following examples, which are provided by way of illustration and are not intended to be limiting of the present invention.

EXAMPLES

Materials and Methods
Controlled Cortical Impact (CCI)

Mice were anesthetized using 2.5% isoflurane gas in oxygen. A 3-mm diameter craniotomy was performed 0.5 mm rostral and 4 mm lateral from the lambda for the visual cortical injury and 4 mm lateral from the lambda-bregma midpoint for the sensori-motor cortical injury. Using a stereotaxic frame and a 2-mm impactor tip, a 2-mm cortical deformation injury was applied (3.00 m/s with 30 s dwell time). After injury, Buprenorphine anesthetic (0.05 mg/kg, s.c. in 1 mL sterile normal saline) was administered daily for two days after injury. Enrofloxacin antibiotic (2.5 mg/kg, s.c. in 1 mL sterile normal saline) was administered daily for three days after injury to reduce the risk of infection.

Closed Head Injury (CHI)

Anesthesia was induced using 2.5% isoflurane gas in oxygen. Using a custom made 38×27×27 $cm^3$ four-sided acrylic stage and an affixed acrylic guide tube, a 240-g weight was dropped on the anesthetized mice from a distance of 1.4 m. The righting time was recorded immediately after the injury. After injury, Buprenorphine anesthetic (0.05 mg/kg, s.c. in 1 mL sterile normal saline) was administered daily for two days after injury. Enrofloxacin antibiotic (2.5 mg/kg, s.c. in 1 mL sterile normal saline) was administered daily for two days after injury to reduce the risk of infection.

Nanoparticle Injection

PLGA-COOH (DEGRADEX® Phosphorex; carboxylated poly(D,L-lactide-co-glycolide) nanoparticles with an L/G ratio of 50/50 and MW of 30,000) were diluted in sterile normal isotonic saline to a final concentration of 4.7 mg/ml, and 200 µl of the dilute nanoparticles was injected via tail vein 2-3 hours after TBI. Each nanoparticle group animal received $4 \times 10^9$ nanoparticles per injection (1.4 mg/kg). Additional injections were performed at 24 and 48 hours post injury. Control animals received equivalent volume injections of normal isotonic saline at the same time points.

Ladder Rung Walking Test

Mice were habituated with a custom-made ladder rung apparatus for 3 minutes each of the seven days before injury. For post-injury testing, each mouse performed three trials, with 5 min of rest, of crossing the ladder rung while being video-recorded. Each video was played back in slow-motion to count the number of foot slips. A random pattern of ladder rungs was used in each day of testing to ensure the animals were not learning the rung placements.

Visual Evoked Potentials (VEPs)

Anesthesia was induced in an induction chamber and maintained with 2.5% isoflurane gas in oxygen using a nose cone. Mouse body temperature was maintained at 37° C. and monitored with isothermal heating pad and rectal thermometer, respectively. A 0.2% atropine solution was used to maximally dilate the pupil. A 25-gauge needle with a silver chloride wire electrode was applied subcutaneously in the midline of the occiput and another electrode was utilized as the reference electrode placed in the snout. Using a dark Faraday-cage and covering the contralateral eye with a patch, diffuse light flashes were applied to the ipsilateral eye (33 lux, 2 Hz) fed through the cage with a fiber optic cable. The VEP amplitudes were recorded through a low pass filter (1 to 500 Hz with a 60 Hz notch filter) and operational amplifier with 10,000 gain fed through A-D converter and analyzed on the workstation. After ten trials, the opposite eye was stimulated and VEPs were recorded.

Flow Cytometry

As previously described (Jeong et al. Neurobiology of disease. 2017; 108:73-82), mice were anesthetized with 50 mg/kg pentobarbital and followed by cardiac perfusion with 30 mL of PBS. For CCI, the injured section of brain (3 mm³ lesional/perilesional area) was micro-dissected at 72 hours after injury. For CHI experiments, whole brain tissue was processed at 72 hours after injury as well. In both instances, 5 mice per experiment were pooled to perform cell analysis by flow cytometry. Injured sections or whole brains were minced with a razor, pushed through a 100 µm filter and digested at 37° C. for 60 min in a PBS solution containing 40 U/mL of Liberase R1 (Roche) and 50 mg/mL DNase I. The resulting cellular suspension was re-suspended in 30% Percoll, overlayed onto 70% Percoll and centrifuged at 1000 rpm for 25 min at 25° C. The cells at the interfaced were collected, washed, re-suspended in FACS buffer (PBS with 2% FCS) and counted. The number of cell subpopulations in the CNS were determined by multiplying the percentage of lineage marker-positive cells by the total number of mononuclear cells isolated from the injured brain/section.

In order to carry out flow cytometry analysis, the Fc receptors were initially blocked using anti-mouse CD16/32 (0.25 µg). Cells were then stained for 30 min at 4° C. using the specified antibodies. Cells were acquired on a BD Canto II and analyzed using BD FACSDiva version 6.1 software.

Western Blots

Mice were euthanized via $CO_2$ inhalation. The lesion and peri-lesional brain region was dissected and lysed in Tissue Protein Extraction Reagent (T-PER) supplemented with 100×HALT protease inhibitor cocktail with mechanical disruption. Debris was removed by centrifugation at 14000 rpm for 10 min at 4° C. Protein concentration was determined by bicinchoninic acid (BCA) protein assay with a standard curve of bovine serum albumin on a NanoDrop™ 2000/2000c spectrophotometer. Cell lysates were mixed with reducing Laemmli loading buffer and separated by sodium dodecyl sulfate polyacrylamide gel electrophoresis (SDS-PAGE). Blots were transferred to Immobilon-P membranes and washed with TBS-T (0.1% Tween 20). Membranes were incubated with primary antibodies at 4° C. overnight in blocking media (5% Blotto nonfat milk in TBS-T). Primary antibodies used were: GAPDH (Millipore MAB374, 1:1000), GFAP (DAKO Z0334, 1:1000). Primary antibodies were visualized using horseradish peroxidase (HRP)-conjugated secondary antibodies at 1:1000 dilution. Blots were developed using ECL Western Blotting Substrate and Amersham HyperFilm ECL. Membranes were stripped and re-probed using Restore Western Blot Stripping Buffer. Western blot films were scanned using a CanoScan 9000F scanner and the resulting .tif format images quantified using the Analyze Gels tool in Fiji Is Just ImageJ.

Lesion Volume Quantification Via Cryosectioning

Mice were euthanized via $CO_2$ inhalation and transcardially perfused with ice cold PBS followed by 4% formaldehyde in PBS. Brains were dissected and post-fixed for 2 hours in 4% formaldehyde at 4° C. Samples were dehydrated overnight in 30% sucrose at 4° C. and then embedded in O.C.T. matrix (Optimal Cutting Temperature by Tissue-Tek). Starting at 5 mm from the rostral pole, 14 µm cryostat sections were taken at 140 µm intervals with each succeeding section collected from 1-6 slides and repeated until 6 sections filled all 6 slides so that the entire lesion was represented by each slide. Slides #1 and #4 were imaged and lesion areas on individual sections were calculated by approximating the native cortical outline and reconstructing and extrapolating volumes from serial sections. These areas were then multiplied by the intervening distance between sections to extrapolate the 3-D lesion volumes.

Immunohistochemistry

Slides were washed in PBS-T (0.05% Triton X-100) and incubated with primary antibodies at 4° C. overnight in blocking media (5% normal donkey serum in PBS-T). Primary antibodies used were: GFAP (DAKO Z0334, 1:1000; Abcam ab4674, 1:1000). Primary antibodies were visualized with Alexa 647 (far red), 594 (red), and 488 (green) Alexa Fluor conjugated secondary antibodies at 1:1000 dilution (Life Technologies). Nuclei were visualized with DAPI at 1:2000 dilution. Stained sections were mounted in ProLong Gold. Images were acquired with a Leica SP5 AOBS 2-photon equipped confocal scope. Note that none of the images presented here were acquired in 2-photon mode. Large format images were stitched using the native Leica Application Suite-Advanced Fluorescence software.

Immunohistochemistry Image Quantification

Quantification of immunofluorescence images was performed by blinded investigators. Images were quantified using the Fiji open source bioimage software to obtain intensities, astrocyte areas, cell counts.

MRI Acquisition

After induction of anesthesia with 2% isoflurane, each mouse was scanned using a 7T Clinscan MRI instrument using a clinical-grade software platform. Respirations, body temperature, and heart rate were continuously surveilled and checked with an MRI-compatible physiological monitoring system throughout the imaging session with anesthesia continuously delivered through a nose cone. T2-weighted and T2*/R2* imaging sequences were employed with corresponding experiments. For T2*/R2* sequences, a gradient multi-echo 3D (MGRE3D) sequence was used to acquire the maps using the following MR parameters Flip Angle=10; TR=80 msec; multiple values of TE=2.7, 6.63, 10.56, 14.49, 18.42, 22.35, 26.28, 30.21, 31.14 msec. The spatial resolution was chosen to be ~180 micron isotropic.

MRI Analysis

All analyses were done by blinded investigators using the generated metadata and the freeware image processing software package ITK SNAP (http://www.itksnap.org/). Ventricular volumes were quantified by thresholding the ventricles (CSF) to measure the precise 3-D volume of the highlighted regions. To measure the lesion volumes and control for systemic trauma-induced hydrocephalus, the cavitary regions of both sides of the brain were isolated in coronal reconstructions and the brain matter volume of the injured (left) side was subtracted from the brain matter volume of the uninjured (right) side. To measure the R2*-hyperintense regions, the same thresholding parameters were employed on the corresponding sequence files and tabulated with ITK-SNAP. For further 3-D reconstruction, opensource MeshLab freeware (http://www.meshlab.net) was employed to differentially color the ventricle and brain matter meshes. 3-D reconstructed videos were made using screen recording software (FlashBack Express Recorder, https://www.flashbackrecorder.com/express/) while stereotypically manipulating the emerged mesh images.

Statistics

Data were analyzed using GraphPad Prism software (version 5.04), and statistical significance was assigned at a predetermined cutoff of $p<0.05$. Comparison between any pair of experimental groups was performed using Student's t-test. Comparisons between 3 or more groups were conducted using one-way ANOVA with Tukey's Multiple Comparison post-hoc test. All data are presented as mean±standard error of the mean (SEM) unless otherwise noted.

Figure 2:
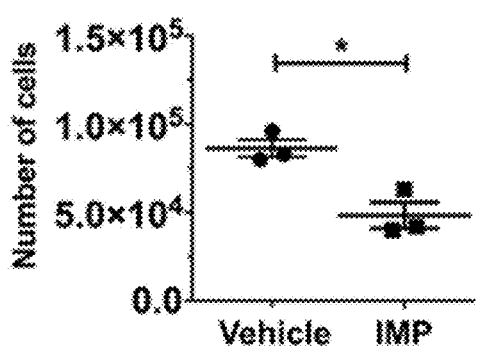
FIG. 2 depicts total number of cells in vehicle- and nanoparticle-treated (IMP-treated) animal lesion areas from the experiment described in FIG. 1.
Figure 3:
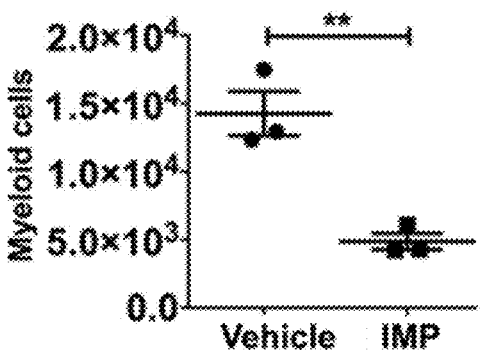
FIG. 3 depicts cell numbers from myeloid cells in vehicle- and nanoparticle-treated animal lesion areas from the experiment described in FIG. 1.
Figure 4:
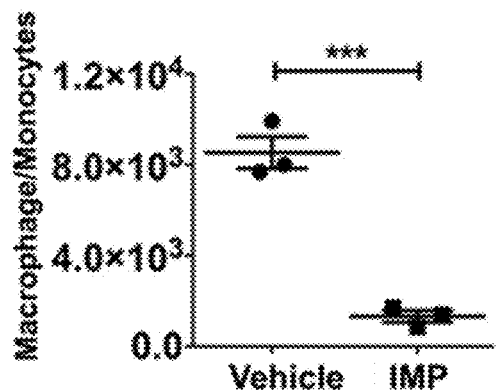
FIG. 4 depicts cell numbers from macrophages/monocytes in vehicle- and nanoparticle-treated animal lesion areas from the experiment described in FIG. 1.
Figure 5:
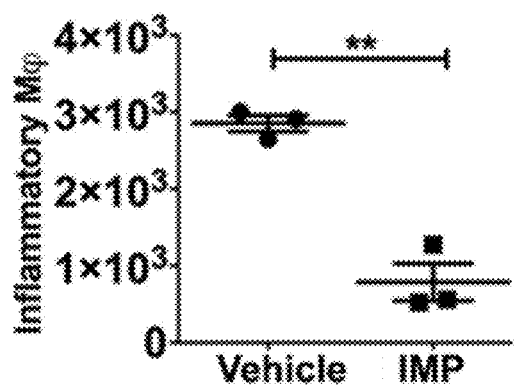
FIG. 5 depicts cell numbers from pro-inflammatory macrophages in vehicle- and nanoparticle-treated animal lesion areas from the experiment described in FIG. 1.
Figure 6:
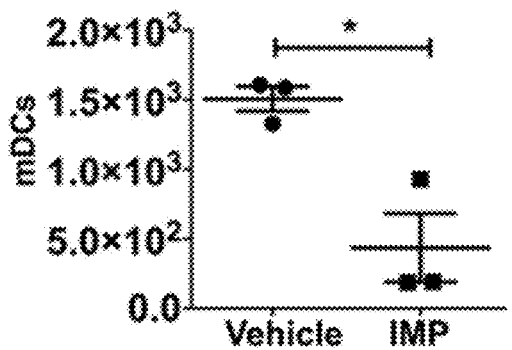
FIG. 6 depicts cell numbers from dendritic cells (mDCs) in vehicle- and nanoparticle-treated animal lesion areas from the experiment described in FIG. 1.
Figure 7:
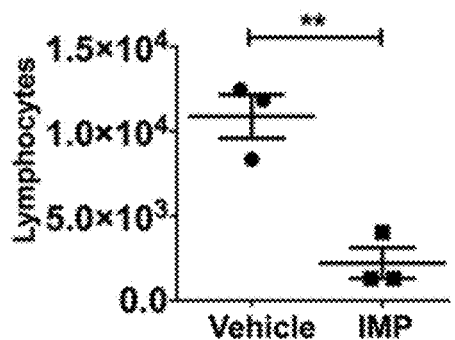
FIG. 7 depicts cell numbers from lymphocytes in vehicle- and nanoparticle-treated animal lesion areas from the experiment described in FIG. 1.
Figure 8:
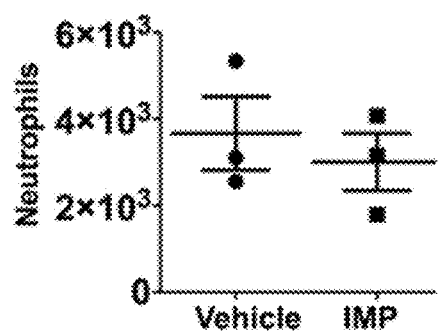
FIG. 8 depicts cell numbers from neutrophils in vehicle- and nanoparticle-treated animal lesion areas from the experiment described in FIG. 1. The absolute number of live cell events for FIGS. 2-8 were detected by flow cytometry using the cell-specific gating from a 3-mm$^3$ lesional/perilesional area that was microdissected at 72 hours after CCI injury.
Figure 9:
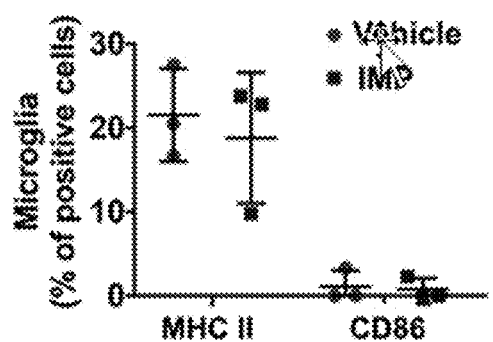
FIG. 9 depicts MHC II expression and CD86 expression in microglia in vehicle- and nanoparticle-treated animal lesion areas from the experiment described in FIG. 1.
Figure 10:
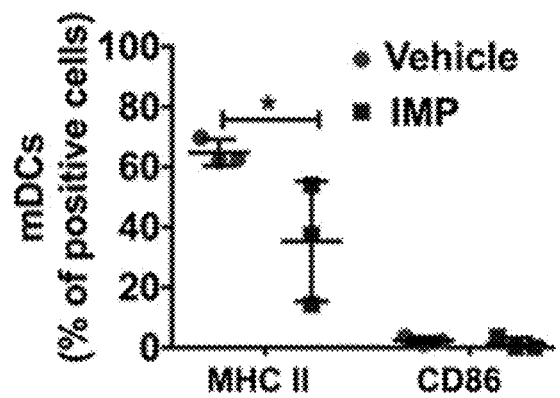
FIG. 10 depicts MHC II expression and CD86 expression in mDCs in vehicle- and nanoparticle-treated animal lesion areas from the experiment described in FIG. 1.
Figure 11:
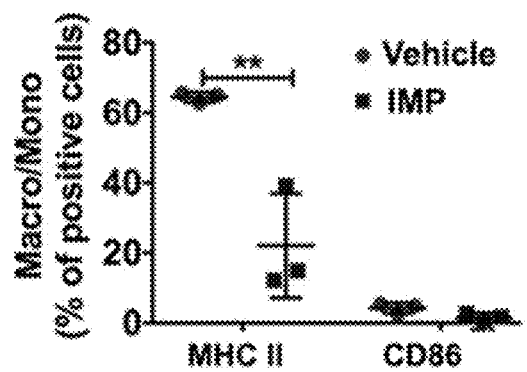
FIG. 11 depicts MHC II expression and CD86 expression in macrophages/monocytes in vehicle- and nanoparticle-treated animal lesion areas from the experiment described in FIG. 1.
Figure 12:
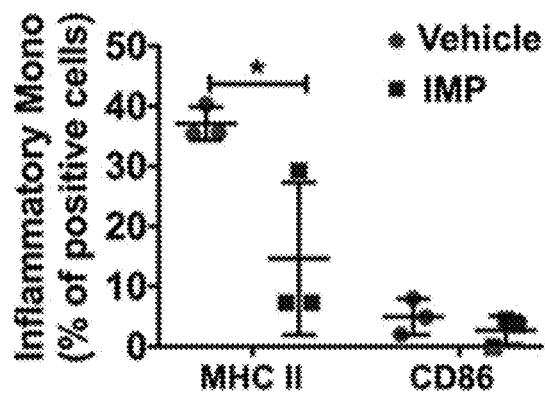
FIG. 12 depicts MHC II expression and CD86 expression in inflammatory monocytes in vehicle- and nanoparticle-treated animal lesion areas from the experiment described in FIG. 1.
Figure 13:
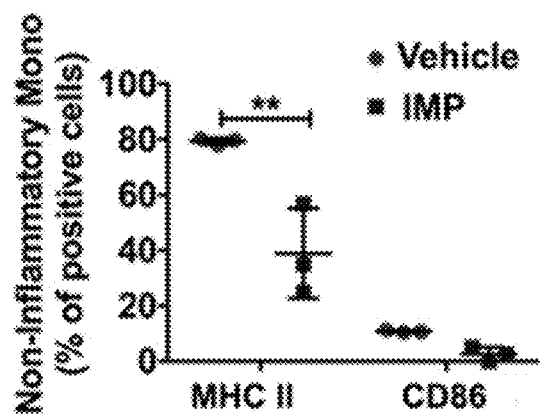
FIG. 13 depicts MHC II expression and CD86 expression in non-inflammatory monocytes in vehicle- and nanoparticle-treated animal lesion areas from the experiment described in FIG. 1.
Figure 14:
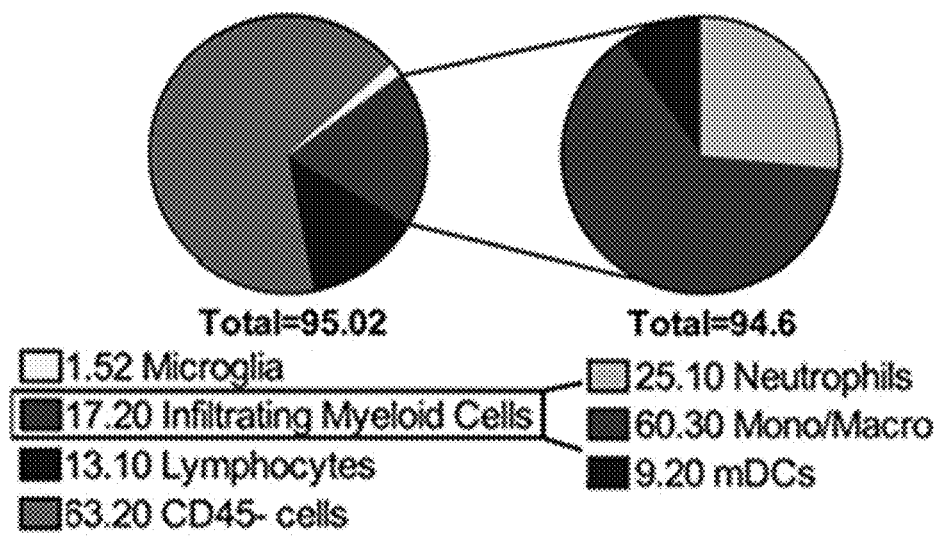
FIG. 14 depicts a pie chart representing all pertinent live cell recorded events compartmentalized by specific cell types and further sub-analysis of the populations of myeloid cells in the lesion area in vehicle-treated animals from the experiment described in FIG. 1.
Figure 15:
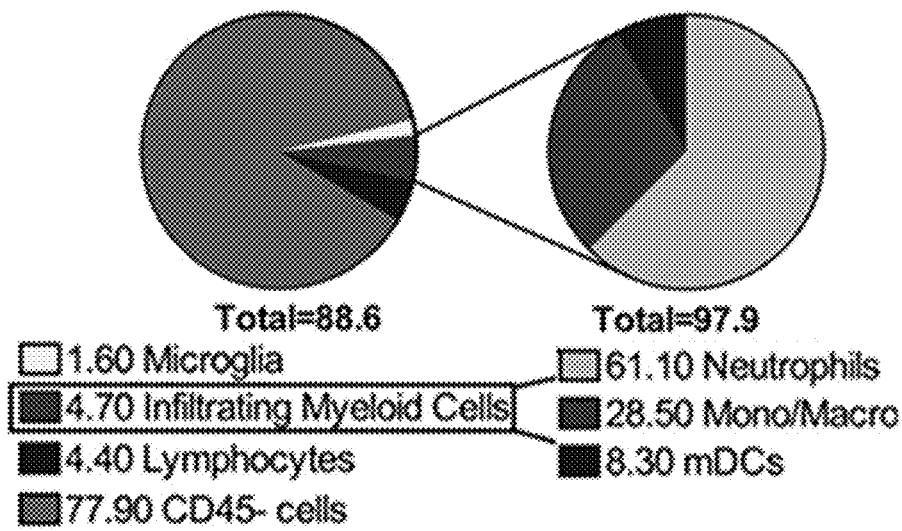
FIG. 15 depicts a pie chart representing all pertinent live cell recorded events compartmentalized by specific cell types and further sub-analysis of the populations of myeloid cells in the lesion area in nanoparticle-treated animals from the experiment described in FIG. 1. All statistics shown in FIGS. 1-15 were by two-tailed t-test with $\alpha$=0.05. *p<0.05, p<0.01, *p<0.001. Myeloid cells: $CD45^{hi}$ $CD11b^+$, Macrophages/Monocytes: $CD45^{hi}$ $CD11b^+$ $Ly6G^-$ $CD11c^-$; Inflammatory monocytes (inflammatory $\varphi$): $CD45^{hi}$ $CD11b^+$ $Ly6G^-$ $CD11c^-$ $Ly6c^{hi}$; Non-inflammatory monocytes (non-inflammatory $\varphi$): $CD45^{hi}$ $CD11b^+$ $Ly6G^-$ $CD11c^-$ $Ly6c^{lo}$; Dendritic cells (mDCs): $CD45^{hi}$ $CD11b^+$ $Ly6G^-$ $CD11c^+$; Neutrophils: $CD45^{hi}$ $CD11b^+$ $Ly6G^+$; Lymphocytes: $CD45^{hi}$ $CD11b^-$; Microglia: $CD45^{hi}$ $CD11b^+$ $Ly6C^-$. Sample size: n=3 for each group. Each data point, n, is composed of 5 animals' microdissected lesion areas pooled together.

Example 1. Study of Effect of Immunomodulatory Nanoparticle (IMP) Treatment on Immune Cell Population in the Lesion Area in CCI Model PLGA-COOH was administered intravenously via lateral tail-vein injection 2 hours after controlled-cortical impact (CCI), a clinically relevant time-point regarding time to intervention, with additional boluses at 24 and 48 hours after the injury (FIG. 1). At 72 hours post injury (hpi), a microdissected, 3-mm³ lesional/perilesional area was examined by flow cytometry using cell specific gating strategies. IMP treatment not only reduced the number of cells in the lesion area by 44.0% (FIG. 2), but also drastically changed the number of specific cell types. There was an 84.5% decrease in infiltrating macrophages/monocytes and a 65.8% decrease in overall myeloid lineage cells after IMP treatment (FIGS. 3, 4, 14, and 15). Further, the phenotype of the monocytes that did infiltrate into the lesion site also was altered by the treatment. IMP treatment reduced the number of inflammatory monocytes (determined by the level of Ly6C expression) by 72.4% (FIG. 5). Notably, the numbers of infiltrating lymphocytes and mDCs were significantly reduced (FIGS. 6 and 7), but the number of brain-infiltrating neutrophils was not reduced by IMP treatment (FIG. 8). Moreover, MHC II expression in monocytes, macrophages and dendritic cells (mDCs) was markedly reduced in the IMP treatment animals (FIGS. 9-11). Thus, in addition to reducing the numbers of myeloid lineage cells, IMP treatment skewed the cells towards a more M2/anti-inflammatory phenotype. IMP-treated mice had a corresponding increase in the numbers of myeloid cells in their spleens.

Example 2. Examination of Tissue Death after IMP Treatment in CCI-TBI Animals

Figure 16:
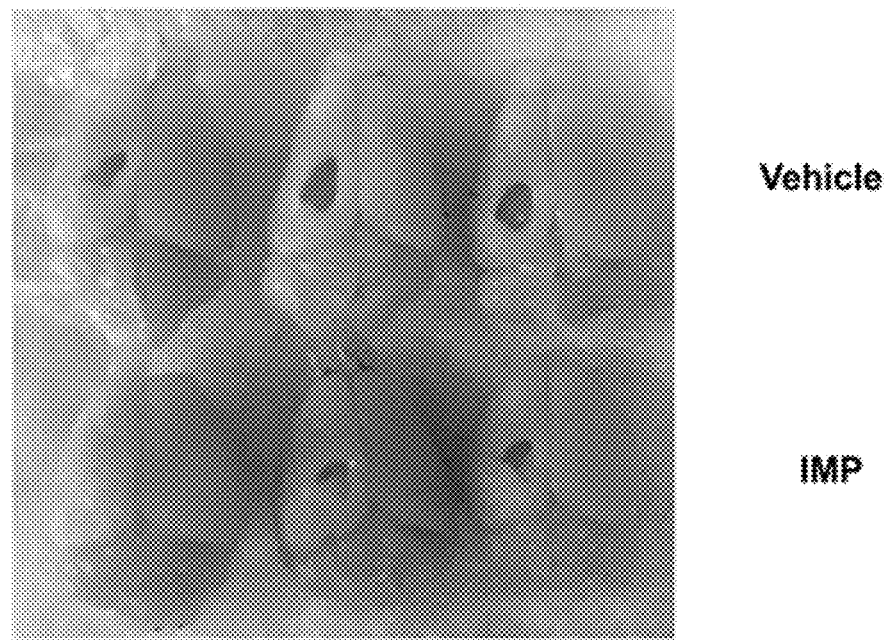
FIG. 16 depicts a representative image of whole brains from vehicle-treated (top row) and nanoparticle-treated (bottom row) mice 10 weeks after visual cortex CCI injury.
Figure 17:
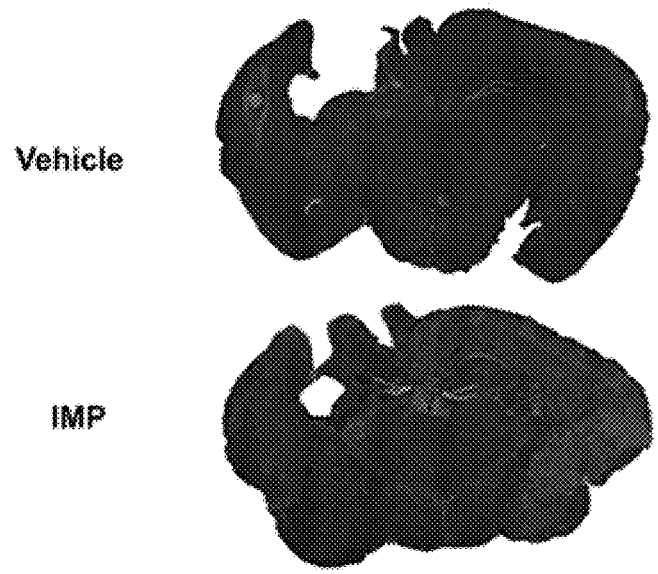
FIG. 17 depicts representative cryostat brain sections of vehicle-(top) and nanoparticle-treated (bottom) animals taken through the center of the lesion cavity. The coronal sections correspond to the top middle (vehicle-treated) and bottom middle brains (nanoparticle-treated) in FIG. 16.
Figure 18:
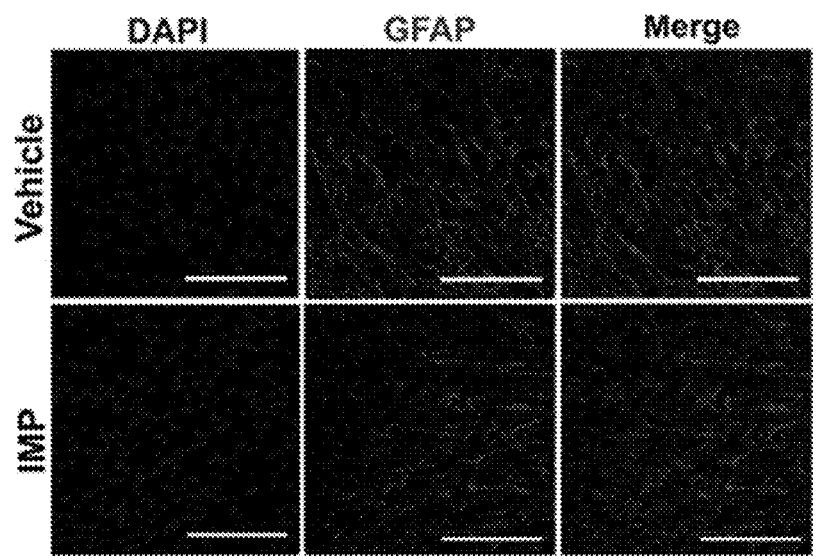
FIG. 18 depicts representative perilesional confocal images stained for GFAP+ astrocytes and DAPI at 10 weeks-post-injury to showcase the attenuated glial scar in the nanoparticle-treated animals.
Figure 19:
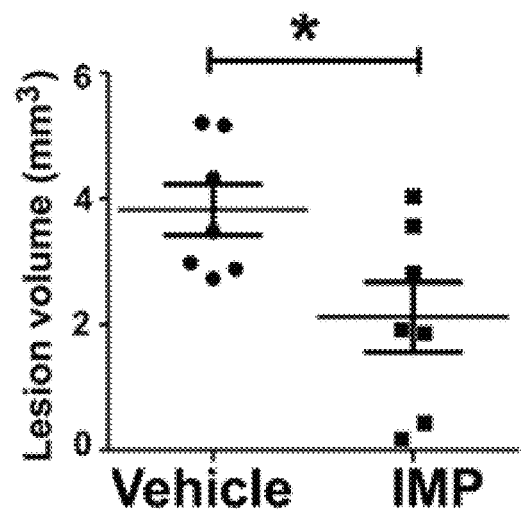
FIG. 19 depicts quantified lesion volumes of the brains in FIG. 16 via cryosectioning and extrapolating to three-dimensions.
Figure 20:
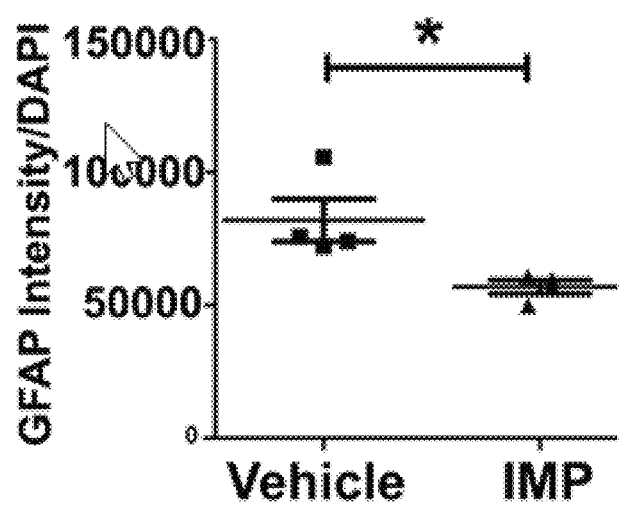
FIG. 20 depicts quantification of the GFAP intensity in perilesional areas in 10 weeks-post-injury vehicle- and nanoparticle-treated animals from FIG. 16. All statistics in FIGS. 16-20 were by two-tailed t-test with $\alpha$=0.05. *p<0.05, p<0.01, *p<0.001. Sample size: n=7 for lesion volumes and n=3 for immunohistochemistry.

Brains were examined 10 weeks-post-injury to determine whether IMP treatment reduced tissue loss after CCI. IMP treatment resulted in a 44.7% reduction in lesion volume compared to vehicle treated animals (FIGS. 16, 17, and 19). The morphology of subcortical structures such as hippocampus and dorsal striatum were partially disturbed in both groups. However, in vehicle treated animals these areas had undergone necrosis with subsequent cavitation, whereas in IMP treated animals, these areas were less disarranged with a more superficial cavity. Chronic perilesional scarring has been shown to be an important factor in inhibiting axonal regeneration and perturbing native tissue architecture both physically and chemically. Because CCI is a focal injury, there was an opportunity to examine the perilesional glial scar at this 10 week time-point. It was found that the glial scar was significantly reduced with lower levels of GFAP in IMP-treated compared to vehicle-treated mice at this chronic time-point (FIGS. 18 and 20).

Figure 21:
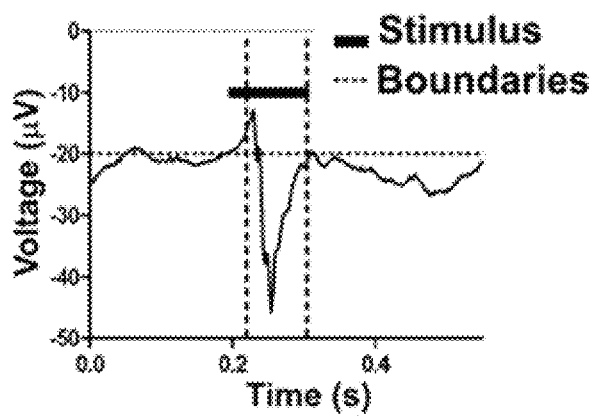
FIG. 21 depicts a representative trace of a single visual evoked potential (VEP) in an uninjured mouse.
Figure 22:
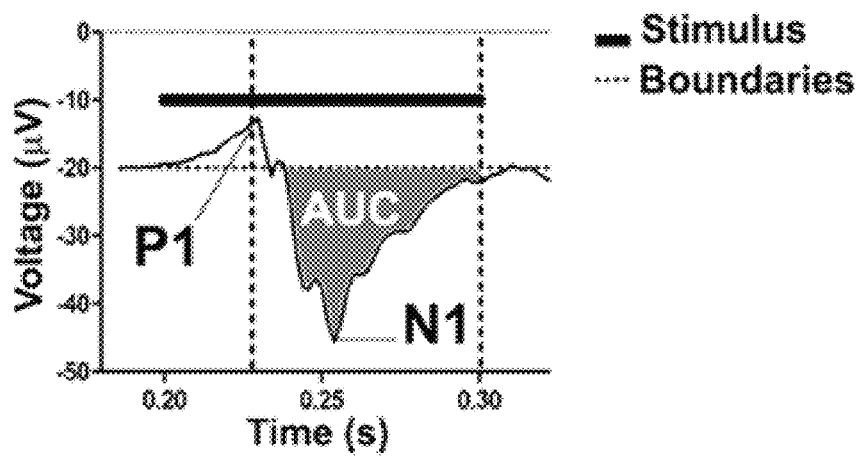
FIG. 22 depicts a time-dilated trace of a VEP to showcase the P1 and N1 waveforms and the bounded area for area under the curve measurements.
Figure 23:
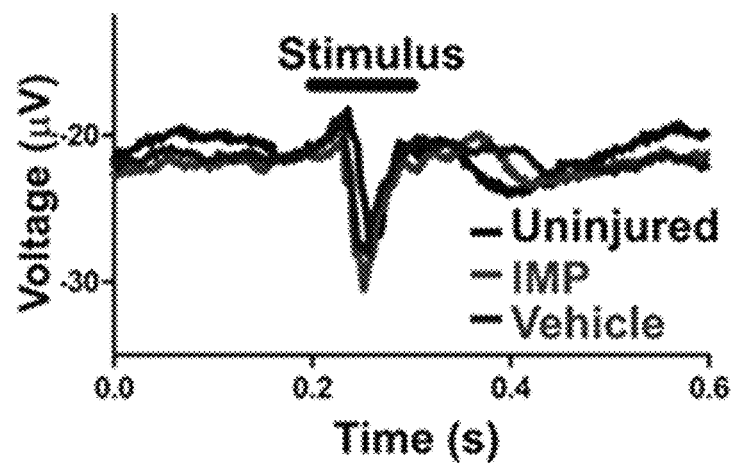
FIG. 23 depicts superimposed grand average VEP waveforms of uninjured, vehicle- and nanoparticle-treated (IMP) groups from the left eye/uninjured right visual cortex.
Figure 24:
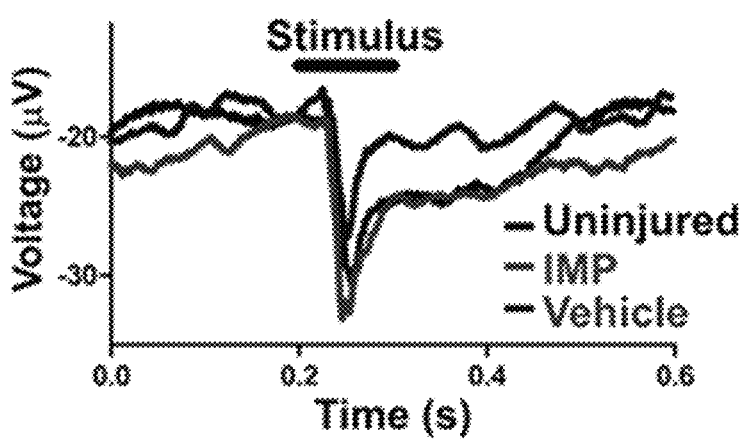
FIG. 24 depicts superimposed grand average VEP waveforms of uninjured, vehicle- and nanoparticle-treated groups from the right eye/injured left visual cortex.
Figure 25:
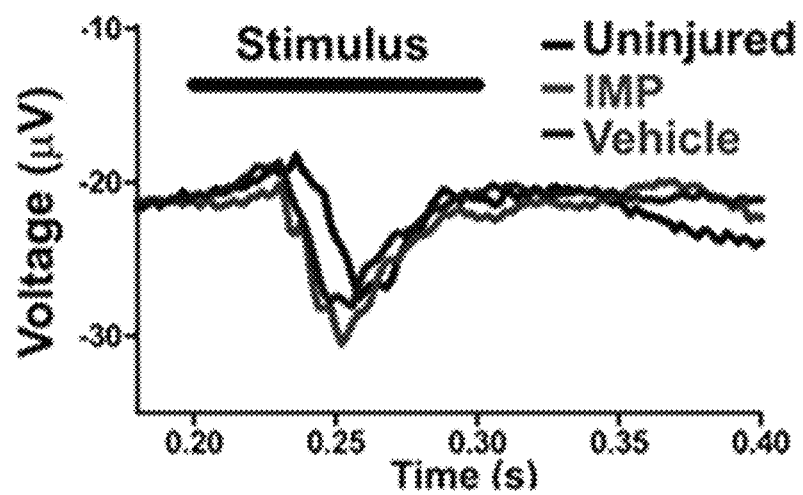
FIG. 25 depicts a time-dilated VEP of FIG. 23.
Figure 26:
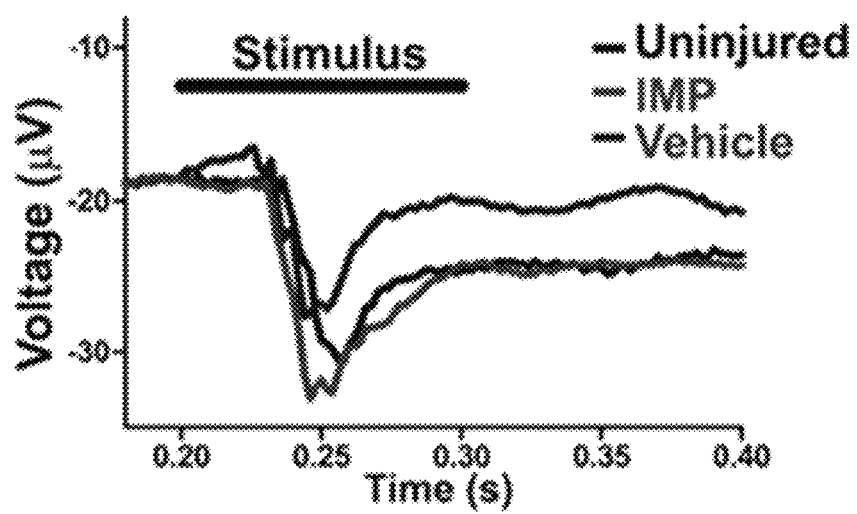
FIG. 26 depicts a time-dilated VEP of FIG. 24.
Figure 27:
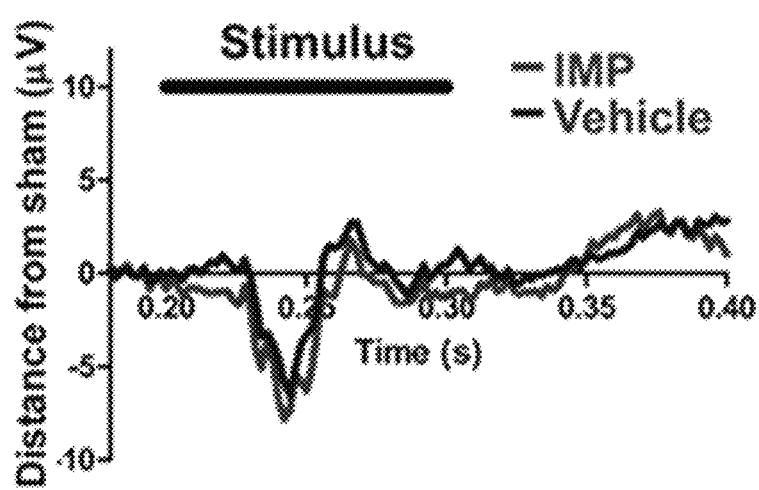
FIG. 27 and FIG. 28 depict transformation with the voltage in the uninjured group becoming the x-axis, and the vehicle-treated and nanoparticle-treated waveforms from FIGS. 25 and 26 expressed in relationship to the uninjured voltage for the left eye (uninjured right visual cortex) in (FIG. 27) and the right eye (injured left visual cortex) in (FIG. 28).
Figure 28:
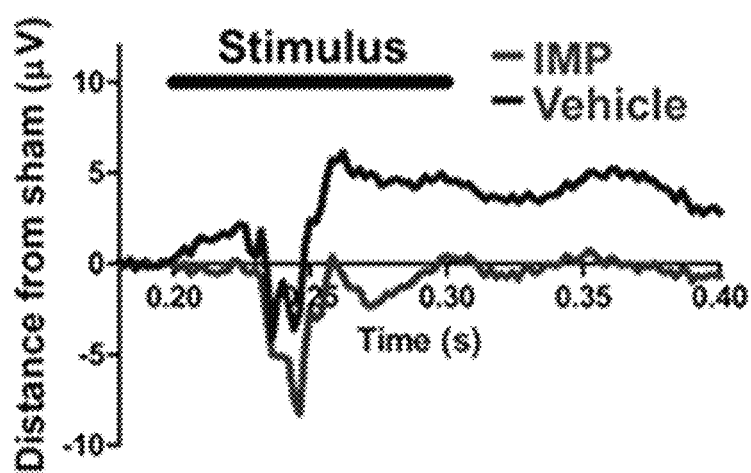
Figure 29:
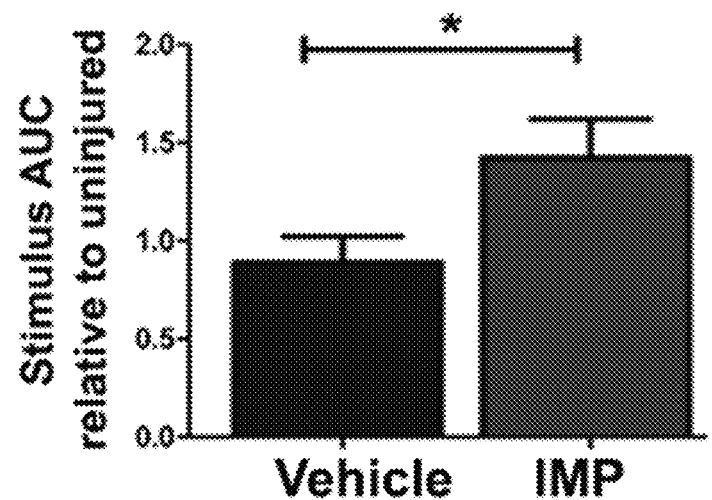
FIG. 29 depicts voltage/potential summated in the time between the P1 response and the end of the stimulus for AUC for the N1 waveform.
Figure 30:
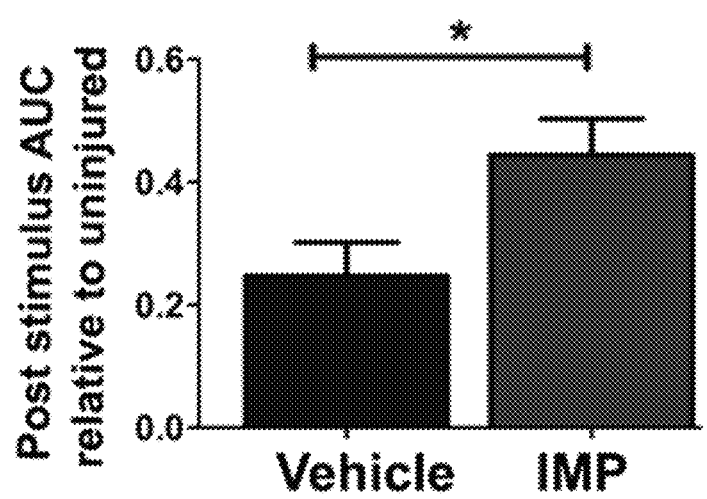
FIG. 30 depicts voltage/potential summated after the end of the stimulus for AUC for the subsequent minor waveforms. Statistics for FIGS. 21-30 were by two-sided t-test with $\alpha$=0.05, *p<0.05, **p<0.01. AUC=area under the curve, $\mu$V=microvolts. Sample size: n=7 in each group.

The function of the cortical tissue preserved by IMP treatment after CCI to the visual cortex was evaluated using visual evoked potentials (VEPs). Each eye was stimulated independently using diffuse flashes, and the VEPs were recorded from the midline of the occiput. Because rodents do not have substantial binocular representations in their visual cortices, the recorded VEPs were attributable to the visual cortex contralateral to the stimulated eye. The latencies of the P1 and N1 peaks were measured to evaluate the VEP conduction, and the area under the curve (AUC) bounded by the waveform was measured to evaluate the extent of potential summation which corresponds to extent of injury (FIGS. 21-22). The AUC was greatly decreased in the injured cortex of the vehicle treated animals compared to the IMP treated group both during the stimulus and succeeding it (FIGS. 23-26 and 29-30). The responses in the cortices of IMP-treated animals did not differ greatly from those in uninjured mice whereas the responses in vehicle-treated mice were greatly reduced (FIGS. 27 and 28). In contrast, there were no differences between the groups in the voltage summation in the uninjured cortex. Further, the latencies for the P1 and N1 waves were not different among the treatment groups indicating the integrity of visual pathways rostral to the damaged cortex. Thus, the cortical tissue preserved by IMP treatment retained physiologic function.

Figure 31:
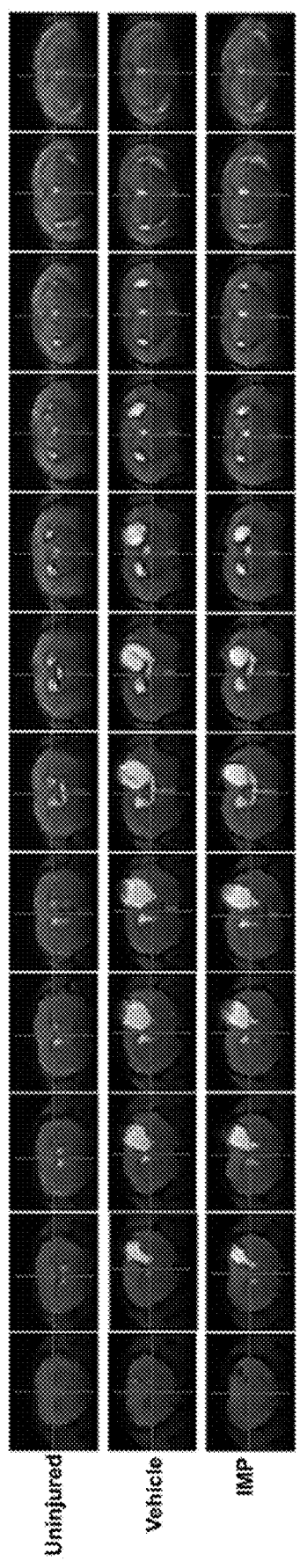
FIG. 31 depicts 16 week-post-injury time-point MRI T2-weighted sequence with serial cuts from the frontal lobe to the caudal aspect of the cerebral cortex to showcase the lesion volume and ventricle size differences among uninjured, vehicle-treated and nanoparticle-treated groups. Sample size: n=4.
Figure 32:
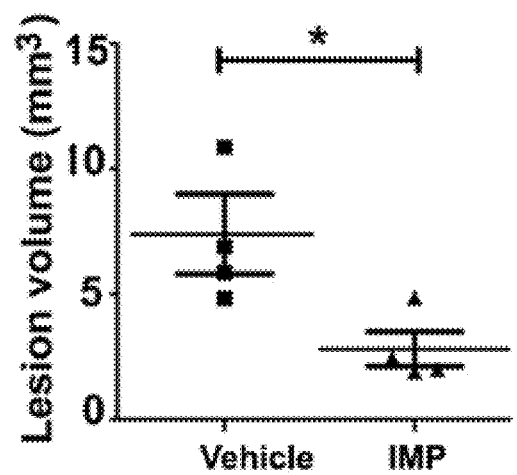
FIG. 32 depicts lesion volume quantification of the vehicle-treated and nanoparticle-treated groups. A two-sided t-test was used for statistics purposes.
Figure 33:
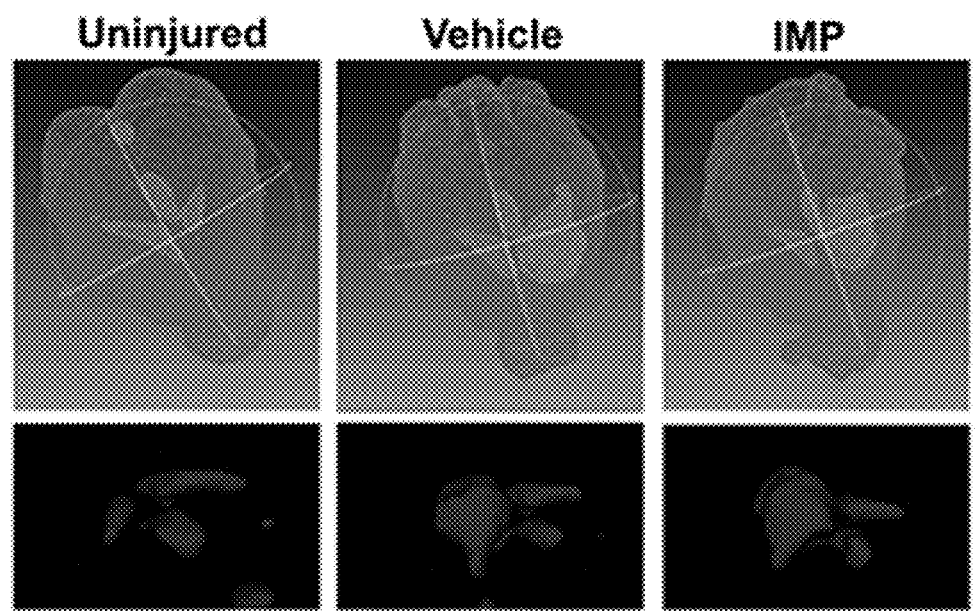
FIG. 33 depicts three-dimensional reconstructions of the brains shown in FIG. 31 (top row) and the respective ventricles (bottom row).
Figure 34:
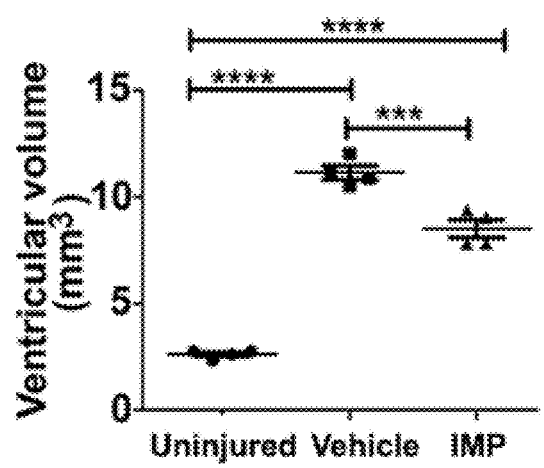
FIG. 34 depicts quantification of the CSF/ventricular volumes of the different groups. One-way analysis of variance (ANOVA) with post-hoc Tukey all comparisons was used for statistics purposes. Sample size: n=4.

Example 3. Assessment of Motor Cortex and Motor Function Following IMP Treatment after CCI The clinically relevant method of magnetic resonance imaging (MRI) was used to assess anatomic changes. When imaged at a chronic 16-week time-point, the IMP-treated animals had significantly reduced lesion volumes compared to the vehicle treated animals (FIGS. 31-33). Ventricular volumes were larger in both injured groups compared to uninjured animals, but the volumes were significantly smaller in IMP-treated compared to vehicle-treated mice (FIG. 34). Therefore, while the tissue loss after injury was sufficient to cause hydrocephalus ex vacuo in these animals, the preservation of brain matter after IMP treatment reduced the development of hydrocephalus.

No difference in fractional anisotropy via diffusion tensor imaging sequences was observed in the MRI studies of CCI-injured animals at 16 weeks-post-injury either (data not shown) which further suggests that the white matter tracts were not different between the treatment groups.

Figure 35:
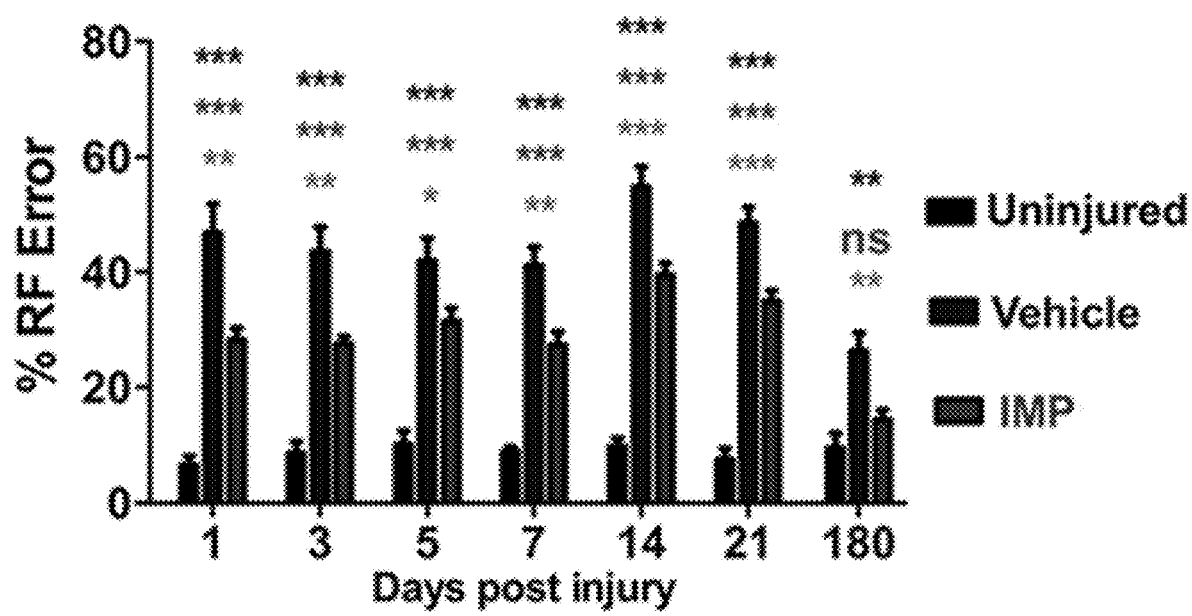
FIG. 35 depicts quantification of ladder rung behavior done at various time points after the CCI measuring percent of right forelimb errors. One-way analysis of variance (ANOVA) with post-hoc Tukey all comparisons was used for statistics purposes. Sample size: n=5-10 in each group.
Figure 36:
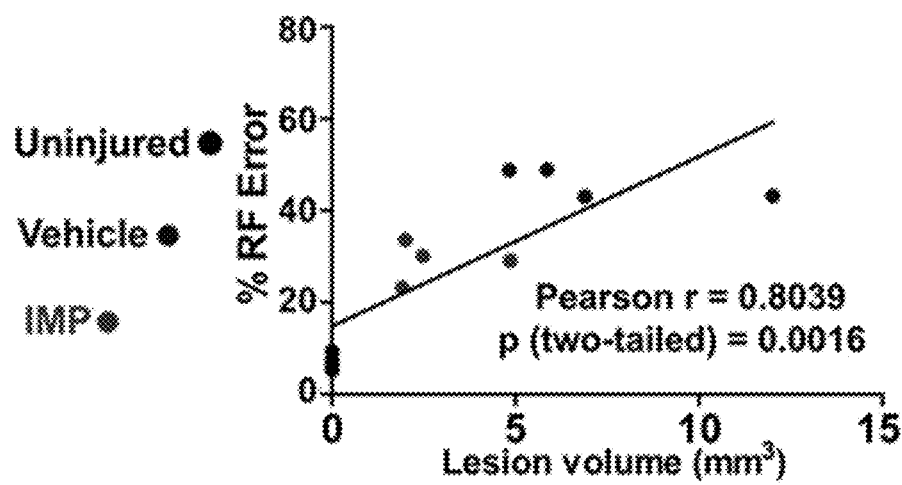
FIG. 36 depicts correlation of lesion volume versus the number of right forelimb (RF) strides. A Pearson correlation was used for statistics purposes. Sample size: n=5-10 in each group.
Figure 37:
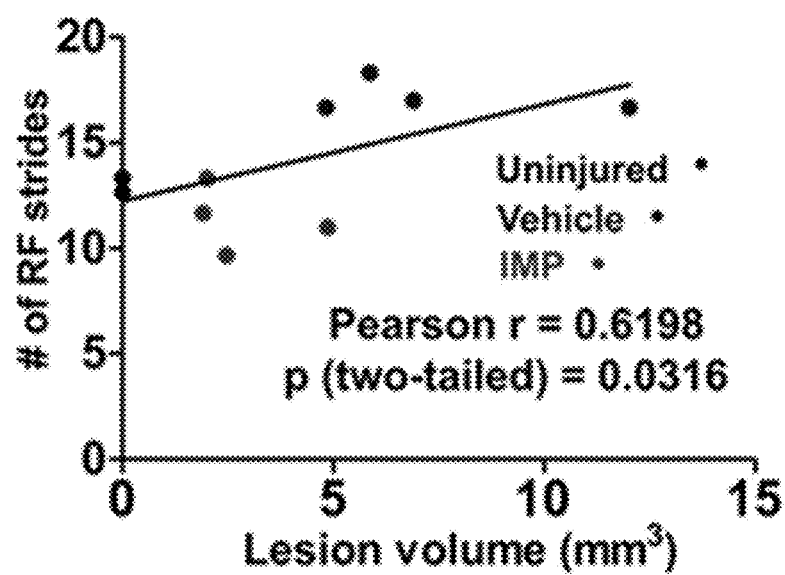
FIG. 37 depicts correlation of lesion volume versus the number of RF strides by Digigait. A Pearson correlation was used for statistics purposes. All statistics in in FIGS. 31-37 used $\alpha$=0.05. *p<0.05, p<0.01, *p<0.001, ****p<0.0001.

To assess motor physiology, the ladder rung walking test was utilized to quantify fine motor behavior in the contralateral forelimb after CCI of the left motor cortex. The IMP treated group had significantly fewer right forelimb (RF) errors than the vehicle treated group at every time point during 3 weeks of ladder rung testing after the injury and at the chronic 6 month (180 day) time-point (FIG. 35). There was a significant correlation between the percent of RF errors on ladder rung testing and lesion volume (FIG. 36). To determine whether IMP treatment resulted in long term improvements in motor function specific to gait, detailed Digigait analysis of the mice at 16 weeks-post-injury was performed. A significant correlation was found between the number of RF strides taken and the end lesion volume (FIG. 37), suggesting decreased motor function on the right side at the chronic time-point.

Example 4. IMP Treatment in Murine CHI Model

Figure 38:
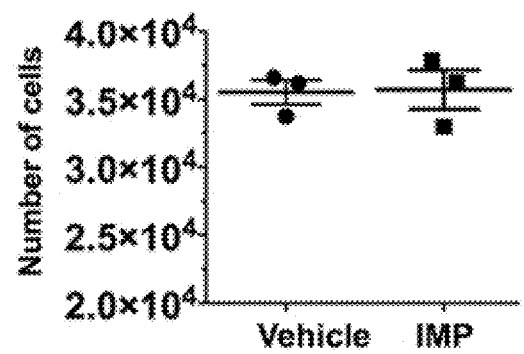
FIG. 38 depicts total number of cells from whole brain tissue 72 hours-post-injury in vehicle- and nanoparticle-treated (IMP-treated) animals in murine closed head drop injury (CHI) model.
Figure 39:
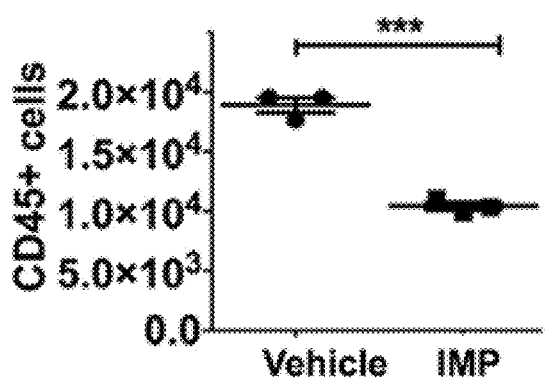
FIG. 39 depicts cell numbers from CD45+ cells from whole brain tissue 72 hours-post-injury in vehicle- and nanoparticle-treated (IMP-treated) animals of FIG. 38.
Figure 40:
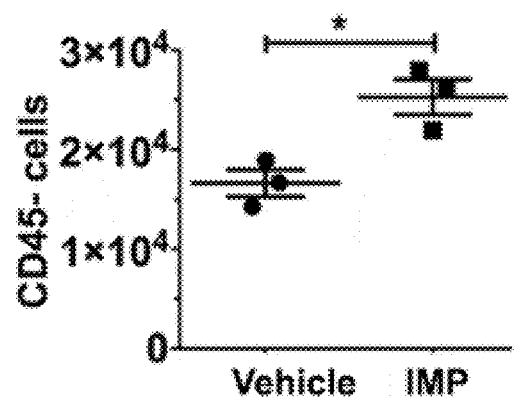
FIG. 40 depicts cell numbers from CD45− cells from whole brain tissue 72 hours-post-injury in vehicle- and nanoparticle-treated (IMP-treated) animals of FIG. 38.
Figure 41:
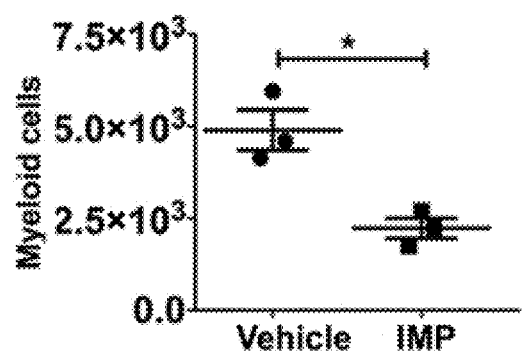
FIG. 41 depicts cell numbers from myeloid cells from whole brain tissue 72 hours-post-injury in vehicle- and nanoparticle-treated (IMP-treated) animals of FIG. 38.
Figure 42:
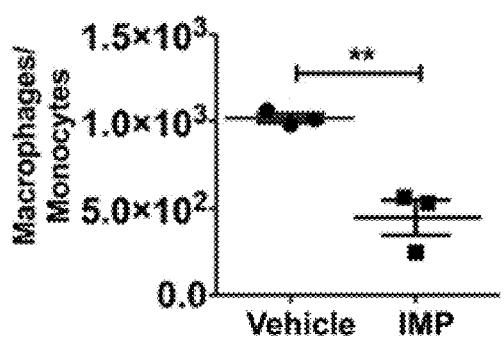
FIG. 42 depicts cell numbers from macrophages/monocytes cells from whole brain tissue 72 hours-post-injury in vehicle- and nanoparticle-treated (IMP-treated) animals of FIG. 38.
Figure 43:
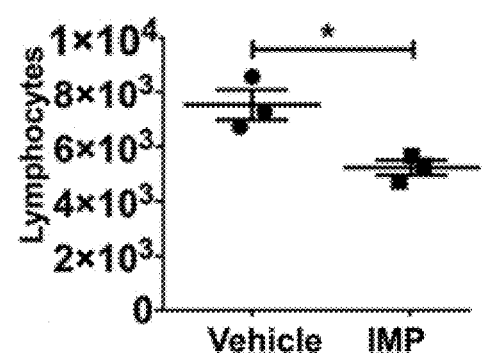
FIG. 43 depicts cell numbers from lymphocytes cells from whole brain tissue 72 hours-post-injury in vehicle- and nanoparticle-treated animals of FIG. 38.
Figure 44:
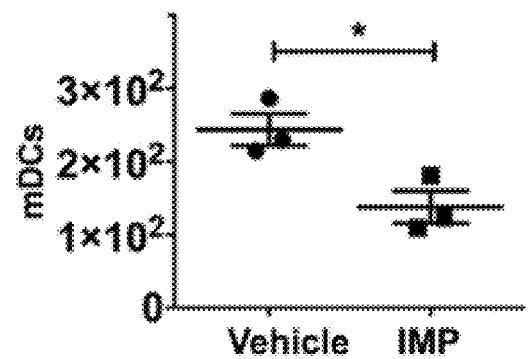
FIG. 44 depicts cell numbers from mDCs cells from whole brain tissue 72 hours-post-injury in vehicle- and nanoparticle-treated animals of FIG. 38.
Figure 45:
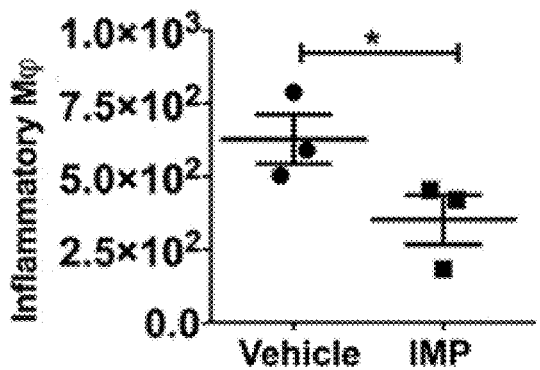
FIG. 45 depicts cell numbers from pro-inflammatory macrophages cells from whole brain tissue 72 hours-post-injury in vehicle- and nanoparticle-treated animals of FIG. 38.
Figure 46:
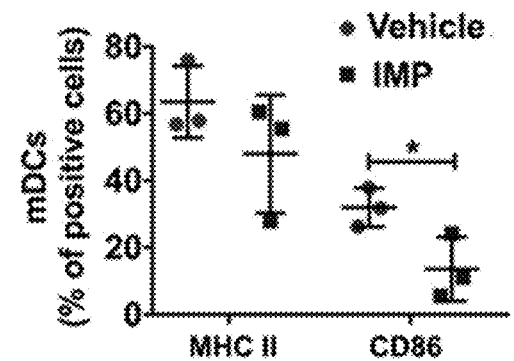
FIG. 46 depicts MHC II expression and CD86 expression in mDCs from whole brain tissue 72 hours-post-injury in vehicle- and nanoparticle-treated animals of FIG. 38.
Figure 47:
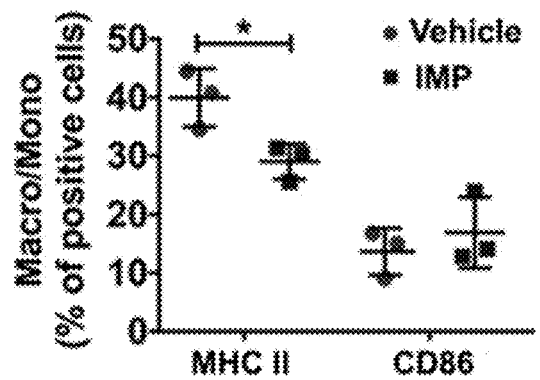
FIG. 47 depicts MHC II expression and CD86 expression in macrophages/monocytes from whole brain tissue 72 hours-post-injury in vehicle- and nanoparticle-treated animals of FIG. 38.
Figure 48:
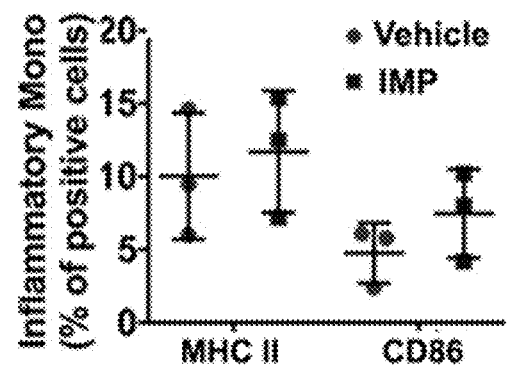
FIG. 48 depicts MHC II expression and CD86 expression in inflammatory monocytes from whole brain tissue 72 hours-post-injury in vehicle- and nanoparticle-treated animals of FIG. 38.

Since most human TBIs are closed head injuries (CHI), the effects of IMP treatment in a more clinically relevant CHI model was examined. CHI leads to less localized damage including contrecoup damage to the contralateral hemisphere. Flow cytometry analysis of cells on whole brain at 72 hours post injury was performed (FIGS. 38-53) to examine the effects of IMP treatment. The total number of cells did not differ between the IMP and vehicle treated mice (FIG. 38). However, IMP treatment significantly reduced the number of CD45+ immune cells by 44.8% (FIG. 39). By contrast, there was a significant increase in live CD45- cells after IMP treatment by 52.0% (FIG. 40) suggesting that fewer neural cells died in the IMP-treated group. Further, IMP treatment significantly reduced the numbers of CD11b myeloid lineage cells by 54.5% (FIG. 41), macrophages/monocytes by 56.1% (FIG. 42), lymphocytes by 30.5% (FIG. 43), and mDCs by 43.4% (FIG. 44), similar to the findings in the CCI model. IMP treatment also significantly reduced the expression of CD86 on mDCs (FIG. 46) and MHC II on monocytes/macrophages (FIG. 47). MHC II and CD86 are both important mediators of inflammation. Thus IMP treatment reduced both the number of infiltrating cells and the inflammatory state of the cells, similar to the findings in the CCI model.

Figure 49:
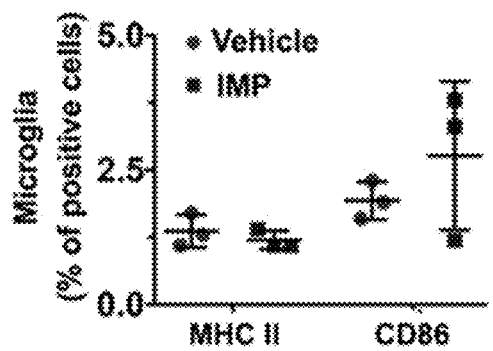
FIG. 49 depicts MHC II expression and CD86 expression in microglia from whole brain tissue 72 hours-post-injury in vehicle- and nanoparticle-treated animals of FIG. 38.
Figure 50:
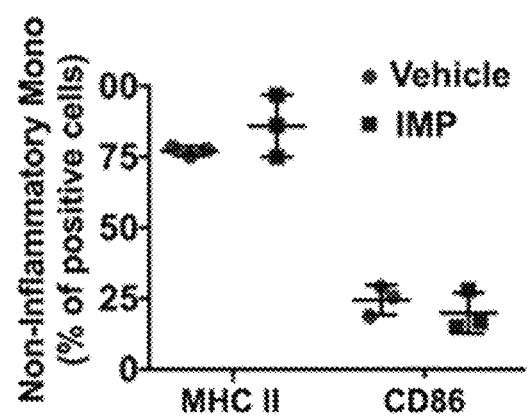
FIG. 50 depicts MHC II expression and CD86 expression in non-inflammatory monocytes from whole brain tissue 72 hours-post-injury in vehicle- and nanoparticle-treated animals of FIG. 38.
Figure 51:
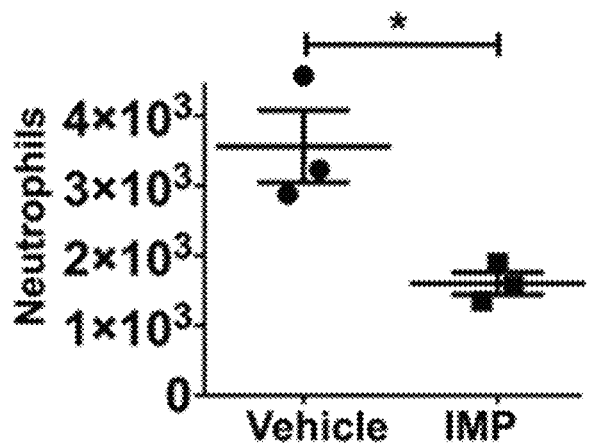
FIG. 51 depicts MHC II expression and CD86 expression in neutrophils from whole brain tissue 72 hours-post-injury in vehicle- and nanoparticle-treated animals of FIG. 38.
Figure 52:
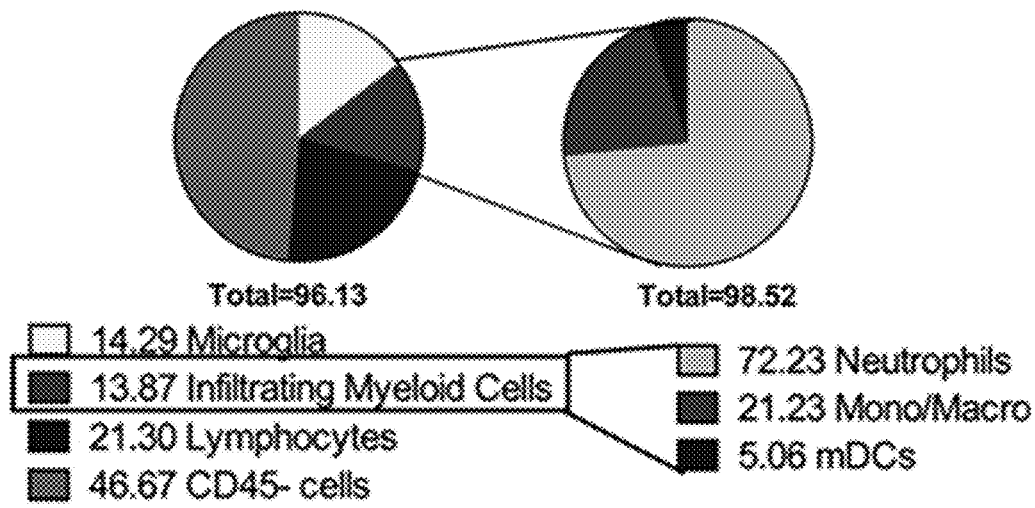
FIG. 52 depicts a pie chart representing all pertinent live cell recorded events compartmentalized by specific cell types and further sub-analysis of the populations of myeloid cells in the lesion area in vehicle-treated animals.
Figure 53:
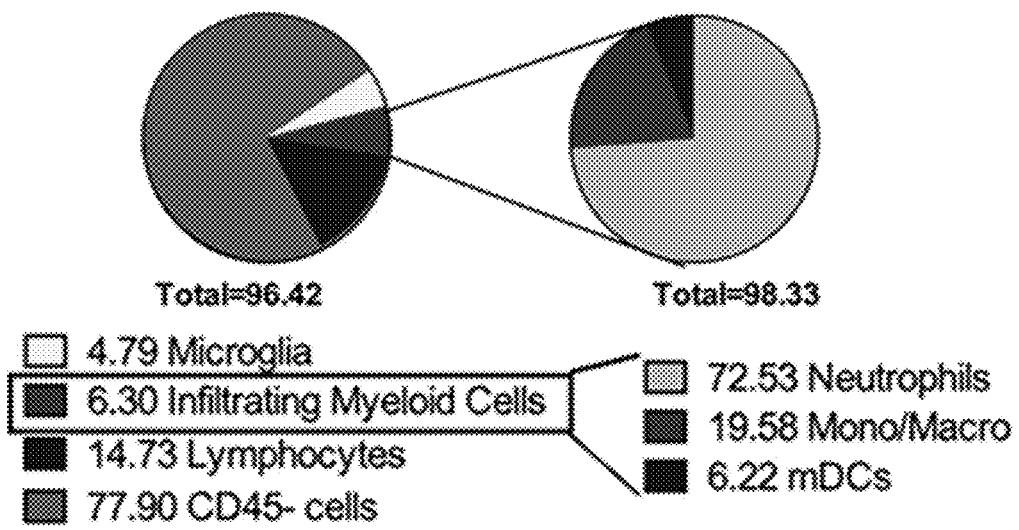
FIG. 53 depicts a pie chart representing all pertinent live cell recorded events compartmentalized by specific cell types and further sub-analysis of the populations of myeloid cells in the lesion area in nanoparticle-treated animals. All statistics shown in this figure were by two-sided t-test with $\alpha=0.05$. $*p<0.05$, $p<0.01$, $*p<0.001$, Myeloid cells: $CD45^{hi}$ $CD11b^+$; Macrophages/Monocytes: $CD45^{hi}$ $CD11b^+$ $Ly6G^-$ $CD11c^-$; Inflammatory monocytes (inflammatory $\varphi$): $CD45^{hi}$ $CD11b^+$ $Ly6G^-$ $CD11c^-$ $Ly6c^{hi}$; Non-inflammatory monocytes (non-inflammatory $\varphi$): $CD45^{hi}$ $CD11b^+$ $Ly6G^-$ $CD11c^-$ $Ly6c^{lo}$; Dendritic cells (mDCs): $CD45^{hi}$ $CD11b^+$ $Ly6G^-$ $CD11c^+$; Neutrophils: $CD45^{hi}$ $CD11b^+$ $Ly6G^+$; Lymphocytes: $CD45^{hi}$ $CD11b^-$; Microglia: $CD45^{int}$ $CD11b^+$ $Ly6C^{lo}$. Sample size: n=3 for each group. Each data point, n, is composed of 5 animals' microdissected lesion areas pooled together.

However, two differences emerged between the CHI and CCI models regarding cell infiltration after IMP treatment: 1) there was a significant decrease in the number of neutrophils found in the brain in the CHI experiments with the IMP treated group (FIG. 57) compared to CCI experiments in which we observed no difference; 2) there was a reduction of microglia number in IMP treated mice in the CHI experiments while there was no difference in microglia in the CCI settings (FIGS. 14, 15, 52, and 53). However, the inflammatory status of microglia did not change after IMP treatment (FIGS. 9 and 49). Overall, the findings in CHI correlate well with the cellular changes observed following IMP treatment in CCI.

Figure 54:
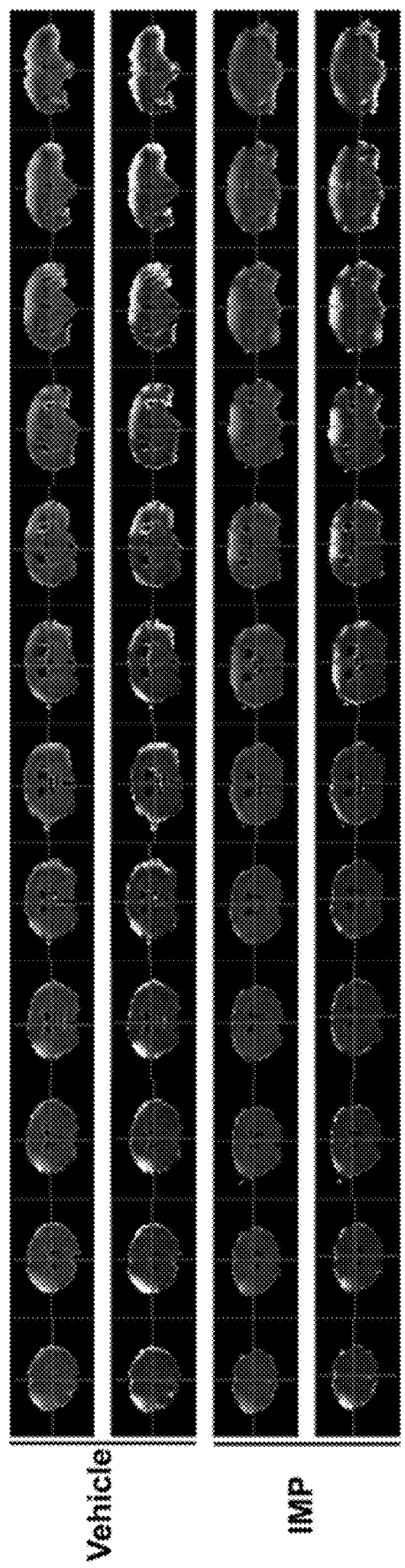
FIG. 54 depicts representative slices of quantitative MM R2*-sequences of vehicle- and nanoparticle-treated animals at 24 hours after CHI-injury.
Figure 55:
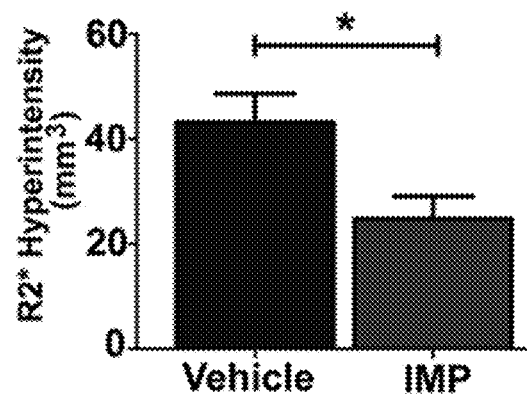
FIG. 55 depicts quantification of the total amount of R2*-hyperintense volume. A two-sided t-test was used for statistics purposes.
Figure 56:
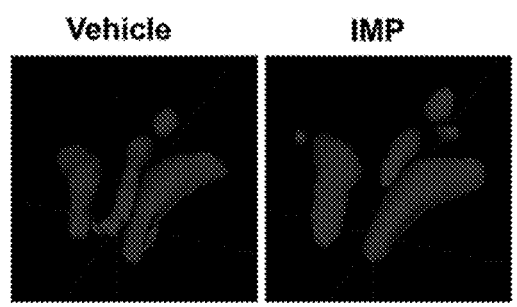
FIG. 56 depicts representative three-dimensional reconstruction of the ventricles of the vehicle- and nanoparticle-treated animals at 24 hours-post-injury showing a decreased ventricle size in the vehicle treated group.
Figure 57:
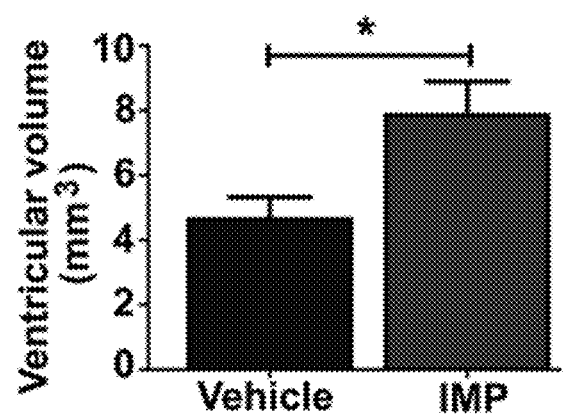
FIG. 57 depicts quantification of the ventricular volumes of the vehicle- and nanoparticle-treated group. A two-sided t-test.
Figure 58:
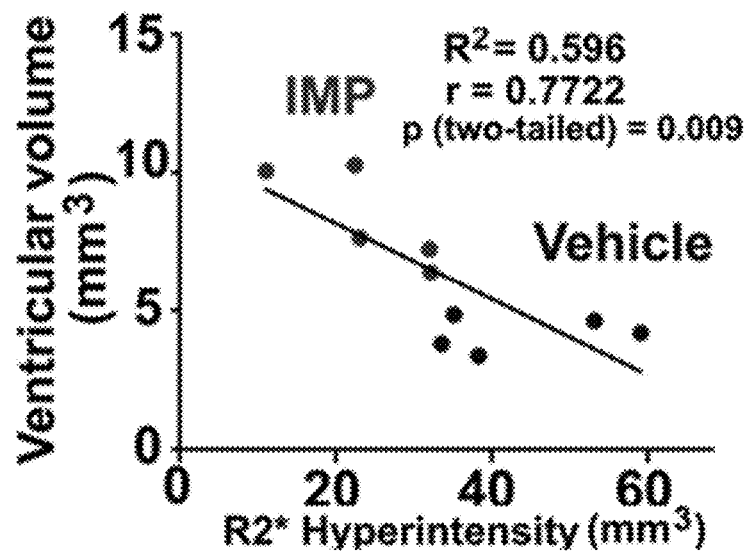
FIG. 58 depicts Pearson correlation of amount of R2 was used for statistics purposes *-hyperintensity volume versus the ventricular volume.
Figure 59:
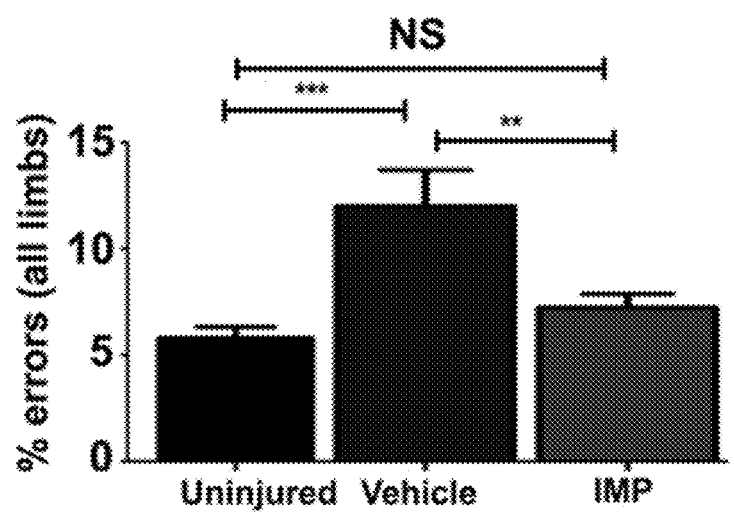
FIG. 59 depicts quantification of the percentage of errors in all limbs at 24 hours-post-injury on ladder-rung assay. A one-way analysis of variance (ANOVA) with post-hoc Tukey all comparisons was used for statistics purposes. All statistics in in FIGS. 54-59 used $\alpha=0.05$. $*p<0.05$, $p<0.01$, $*p<0.001$. NS=not significant.

Example 5. Assessment of Attenuation of Brain Edema and White-Matter Integrity in Closed-Head Injury (CHI) after IMP Treatment The global injury produced in the CHI model leads to edema and increased intracranial pressure in rodents, similar to human injuries. A quantitative $R2^*$-sequencing modality on MRI was used to evaluate tissue edema at 24 hours-post-injury, a time of peak edema. Even with only one infusion of IMP/vehicle at 2 hpi there was attenuated volume of $R2^*$ hyperintensity in the IMP group at 24 hours (FIGS. 54 and 55). In closed head injuries, increased intraparenchymal pressure from edema leads to compression of ventricles with a reduction in their size and increased intracranial pressure (ICP). Therefore, as a surrogate for ICP, magnetic resonance imaging was used to measure the volumes of the ventricles. The vehicle-treated animals had significantly smaller ventricles than the IMP treated animals, implying that these animals had increased ICP (FIGS. 56 and 57). Further, a significant inverse correlation was found between the volume of $R2^*$ hyperintensity and the ventricular volumes (FIG. 58). Finally, since the CHI resulted in damage to both hemispheres, motor function was assessed in all four limbs at 24 hours-post-injury using the ladder rung assay and it was found that the IMP-treated group outperformed the vehicle-treated group (FIG. 59) suggesting an acutely attenuated motor behavior dysfunction with only one IMP infusion.

Para. A. A method of treating traumatic brain injury in a subject in need thereof, the method comprising administering to the subject a therapeutically effective amount of nanoparticles consisting essentially of poly(lactic-co-glycolic acid) (PLGA).

Para. B. The method of Para. A or Para. B, wherein the nanoparticles are carboxylated.

Para. C. The method of Para. A or Para. B, wherein the nanoparticles have a diameter in a range of between about 300 nm and about 1 μm.

Para. D. The method of Para. C, wherein the nanoparticles have a diameter of about 500 nm.

Para. E. The method of any one of Paras. A-D, wherein the nanoparticles are free of any attached or embedded peptide, antigen, or other active agent.

Para. F. The method of any one of Paras. A-E, wherein the nanoparticles consist of PLGA.

Para. G. The method of any one of Paras. A-F, wherein the nanoparticles are administered at least once per day.

Para. H. The method of any one of Paras. A-G, wherein the nanoparticles are administered intravenously.

Para. I. A method of reducing secondary inflammatory damage in the brain after traumatic brain injury in a subject in need thereof, the method comprising administering to the subject a therapeutically effective amount of nanoparticles consisting essentially of poly(lactic-co-glycolic acid) (PLGA).

Para. J. The method of Para. I, wherein the nanoparticles are carboxylated.

Para. K. The method of Para. I or Para. J, wherein the nanoparticles have a diameter in a range of between about 300 nm and 1 μm.

Para. L. The method of Para. K, wherein the nanoparticles have a diameter of about 500 nm.

Para. M. The method of any one of Paras. I-L, wherein the nanoparticles are free of any attached or embedded peptide, antigen, or other active agent.

Para. N. The method of any one of Paras. I-M, wherein the nanoparticles consist of PLGA.

Para. O. The method of any one of Paras. I-N, wherein the nanoparticles are administered at least once per day.

Para. P. The method of any one of Paras. I-O, wherein the nanoparticles are administered intravenously.

Para. Q. A method of limiting lesion volume in the brain after traumatic brain injury in a subject in need thereof, the method comprising administering to the subject a therapeutically effective amount of nanoparticles consisting essentially of poly(lactic-co-glycolic acid) (PLGA).

Para. R. The method of Para. Q, wherein the nanoparticles are carboxylated.

Para. S. The method of Para. Q or Para. R, wherein the nanoparticles have a diameter in a range of between about 300 nm and 1 µm.

Para. T. The method of Para. S, wherein the nanoparticles have a diameter of about 500 nm.

Para. U. The method of any one of Paras. Q-T, wherein the nanoparticles are free of any attached or embedded peptide, antigen, or other active agent.

Para. V. The method of any one of Paras. Q-U, wherein the nanoparticles consist of PLGA.

Para. W. The method of any one of Paras. Q-V, wherein the nanoparticles are administered at least once per day.

Para. X. The method of any one of Paras. Q-W, wherein the nanoparticles are administered intravenously.

Para. Y. A method of attenuating brain edema after closed-head injury in a subject in need thereof, the method comprising administering to the subject a therapeutically effective amount of nanoparticles consisting essentially of poly(lactic-co-glycolic acid) (PLGA).

Para. Z. The method of Para. Y, wherein the nanoparticles are carboxylated.

Para. AA. The method of Para. Y or Para. Z, wherein the nanoparticles have a diameter in a range of between about 300 nm and 1 µm.

Para. AB. The method of Para. AA, wherein the nanoparticles have a diameter of about 500 nm.

Para. AC. The method of any one of Paras. Y-AB, wherein the nanoparticles are free of any attached or embedded peptide, antigen, or other active agent.

Para. AD. The method of any one of Paras. Y-AC, wherein the nanoparticles consist of PLGA.

Para. AE. The method of any one of Paras. Y-AD, wherein the nanoparticles are administered at least once per day.

Para. AF. The method of any one of Paras. Y-AE, wherein the nanoparticles are administered intravenously.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method of treating traumatic brain injury in a subject in need thereof, the method comprising administering to the subject a therapeutically effective amount of nanoparticles consisting essentially of poly(lactic-co-glycolic acid) (PLGA); wherein the nanoparticles are free of any attached or embedded peptide, antigen, or other active agent; and the nanoparticles are administered intravenously.

2. The method of claim 1, wherein the nanoparticles are carboxylated.

3. The method of claim 1, wherein the nanoparticles have a diameter in a range of between about 300 nm and about 1 µm.

4. The method of claim 3, wherein the nanoparticles have a diameter of about 500 nm.

5. The method of claim 1, wherein the nanoparticles are administered at least once per day.

6. The method of claim 1, wherein the PLGA has a MW of 30,000.

7. A method of reducing secondary inflammatory damage in the brain after traumatic brain injury in a subject in need thereof, the method comprising administering to the subject a therapeutically effective amount of nanoparticles consisting essentially of poly(lactic-co-glycolic acid) (PLGA); wherein the nanoparticles are free of any attached or embedded peptide, antigen, or other active agent; and the nanoparticles are administered intravenously.

8. The method of claim 7, wherein the nanoparticles are carboxylated.

9. The method of claim 7, wherein the nanoparticles have a diameter in a range of between about 300 nm and 1 µm.

10. The method of claim 9, wherein the nanoparticles have a diameter of about 500 nm.

11. The method of claim 7, wherein the nanoparticles are administered at least once per day.

12. The method of claim 7, wherein the PLGA has a MW of 30,000.

13. A method of limiting lesion volume in the brain after traumatic brain injury in a subject in need thereof, the method comprising administering to the subject a therapeutically effective amount of nanoparticles consisting essentially of poly(lactic-co-glycolic acid) (PLGA); wherein the nanoparticles are free of any attached or embedded peptide, antigen, or other active agent; and the nanoparticles are administered intravenously.

14. The method of claim 13, wherein the nanoparticles are carboxylated.

15. The method of claim 13, wherein the nanoparticles have a diameter in a range of between about 300 nm and 1 µm.

16. The method of claim 15, wherein the nanoparticles have a diameter of about 500 nm.

17. The method of claim 13, wherein the PLGA has a MW of 30,000.

* * * * *